(12) United States Patent
Beeler et al.

(10) Patent No.: US 10,087,149 B2
(45) Date of Patent: Oct. 2, 2018

(54) SELECTIVE HISTONE DEACETYLASE 8 INHIBITORS

(71) Applicants: TRUSTEES OF BOSTON UNIVERSITY, Boston, MA (US); DANA-FARBER CANCER INSTITUTE, INC., Boston, MA (US)

(72) Inventors: Aaron Beaty Beeler, Cambridge, MA (US); John A. Porco, Jr., Brookline, MA (US); Oscar J. Ingham, Boston, MA (US); James E. Bradner, Weston, MA (US)

(73) Assignees: TRUSTEES OF BOSTON UNIVERSITY, Boston, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 14/763,013

(22) PCT Filed: Jan. 24, 2014

(86) PCT No.: PCT/US2014/012968
§ 371 (c)(1),
(2) Date: Jul. 23, 2015

(87) PCT Pub. No.: WO2014/116962
PCT Pub. Date: Jul. 31, 2014

(65) Prior Publication Data
US 2015/0352079 A1  Dec. 10, 2015

Related U.S. Application Data

(60) Provisional application No. 61/756,292, filed on Jan. 24, 2013.

(51) Int. Cl.
*C07D 249/06* (2006.01)
*A61K 31/4192* (2006.01)
*A61K 45/06* (2006.01)

(52) U.S. Cl.
CPC ........ *C07D 249/06* (2013.01); *A61K 31/4192* (2013.01); *A61K 45/06* (2013.01)

(58) Field of Classification Search
None
See application file for complete search history.

(56) References Cited

U.S. PATENT DOCUMENTS

2005/0159470 A1  7/2005  Bressi et al.
2009/0181943 A1  7/2009  Tessier et al.

FOREIGN PATENT DOCUMENTS

JP  2012-82155 A  4/2012
WO  2011/089995 A1  7/2011

OTHER PUBLICATIONS

Angell et al., Angew. Chem. Int. Ed., 2007, 46, 3649-3651.*
Ito et al. In Cancer Science 94(1), 3-8 (2003).*
STN Registry database entry for CAS RN 958752-74-4; Entered STN Dec. 19, 2007; Accessed Oct. 19, 2016.*
Vannini et al. "Crystal structure of a eukaryotic zinc-dependent histone deacetylase, human HDAC8, complexed with a hydroxamic acid inhibitor" PNAS 101(42):15064-15069 (2004).
Gerard et al. "Synthesis of 1,4,5-trisubstituted-1,2,3-triazoles by copper-catalyzed cycloaddition-coupling of azides and terminal aklynes" Tetrahedron 62:6405-6411 (2006).
Balasubramanian et al., "A novel histone deacetylase 8 (HDAC8)-specific inhibitor PCI-34051 induces apoptosis in T-cell lymphomas", Leukemia 22:1026-1034 (2008).
Bradner et al., "Chemical phylogenetics of histone deacetylases", Nature Chemical Biology 6:238-243 (2010).
Dowling et al., "Structural Studies of Human Histone Deacetylase 8 and Its Site-Specific Variants Complexed with Substrate and Inhibitors", Biochemistry 47(51):13554-13563 (2008).
Rostovtsev et al., "A Stepwise Huisgen Cycloaddition Process: Copper (I)-Catalyzed Regioselective "Ligation" of Azides and Terminal Alkynes", Angewandte Chemie International Edition 41(14):2596-2599 (2002).
Suzuki et al., "Rapid Discovery of Highly Potent and Selective Inhibitors of Histone Deacetylase 8 Using Click Chemistry to Generate Candidate Libraries", Journal of Medicinal Chemistry 55:9562-9575 (2012).
Estiu, "Structural Origin of Selectivity in Class II-Selective Histone Deacetylase Inhibitors" J. Med. Chem. 51:2898-2906 (2008).

* cited by examiner

*Primary Examiner* — Alicia L Otton
(74) *Attorney, Agent, or Firm* — Nixon Peabody LLP

(57) ABSTRACT

Described herein are compounds and pharmaceutical compositions containing such compounds, which inhibit the activity of histone deacetylase 8 (HDAC8). Also described herein are methods of using such HDAC8 inhibitors, alone and in combination with other compounds, for treating diseases or conditions that benefit from inhibition of HDAC8 activity.

18 Claims, 6 Drawing Sheets

SELECTIVE HISTONE DEACETYLASE 8 INHIBITORS

GOVERNMENT SUPPORT

This invention was made with government support under grant no. GM067041 awarded by the National Institutes of Health. The government has certain rights in the invention.

CROSS REFERENCE TO RELATED APPLICATIONS

This application is a 371 National Phase Entry of International Patent Application No. PCT/US2014/012968 filed on Jan. 24, 2014 which claims benefit under 35 U.S.C. § 119(e) of the U.S. Provisional Patent Application Ser. No. 61/756,292 filed on Jan. 24, 2013, the contents of which are incorporated herein by reference in their entirety.

TECHNICAL FIELD

The present disclosure relates generally to compounds, pharmaceutical compositions and medicaments that include such compounds, and methods of using such compounds to inhibit the activity of histone deacetylase 8.

BACKGROUND

As histone proteins bind DNA prior to transcription, their biochemical action plays a critical role in the regulation of gene expression and cellular differentiation. Histone deacetylases (HDACs) are an important family of proteins predominantly responsible for specific posttranslational modifications of histone proteins, the chief organizational component of chromatin. HDACs catalyze the removal of acetyl groups from histones and other cellular proteins. HDAC-mediated deacetylation of chromatin-bound histones regulates the expression of a variety of genes throughout the genome. Importantly, HDACs have been linked to cancer, as well as other health conditions. To date, eleven major HDAC isoforms have been described (HDACs 1-11). HDACs are categorized into two classes. Class I HDACs include HDAC1, HDAC2, HDAC3, HDAC8 and HDAC11. Class II HDACs include HDAC4, HDAC5, HDAC6, HDAC7, HDAC9 and HDAC10. HDAC's are validated targets for a number of disease states, including cancer, neurodegenerative diseases, sickle-cell anemia, muscular dystrophy, and HIV. There are currently two HDAC inhibitors on the market, Vorniostat and Romidepsin. Both are approved for treatment of T-cell lymphoma. However, they are both pan active inhibitors showing very little specificity of binding to HDAC subclasses. Because of this lack of specificity they have a number of side effects.

Non-selective HDAC inhibitors effect deacetylase activity of most, if not all, of the HDACs. The mechanisms of the anticancer effects of SAHA, a non-selective HDAC inhibitor, are not completely understood, and likely result from both altered gene expression and altered function of proteins regulating cell proliferation and cell death pathways. Non-selective HDAC inhibitors, such as SAHA, induce the accumulation of acetylated histone proteins and non histone proteins.

Small molecule HDAC inhibitors that are isoform-selective are useful as therapeutic agents with reduced toxicity and as tools for probing the biology of the HDAC isoforms. The present disclosure is related, in part to small molecules that are selective HDAC inhibitors.

SUMMARY

The present disclosure is based on inventors' discovery of small molecule HDAC inhibitors, which are selective for HDAC8. Accordingly, in one aspect, the disclosure provides a compound of formula (I):

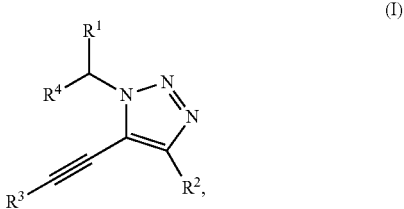

wherein:
$R^1$ is optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, halogen, CN, $CF_3$, $C(O)R^5$, $CO_2R^5$, $C(O)N(R^6)_2$, $OR^5$, $SR^5$, $SOR^5$, $SO_2R^5$, $SSR^5N(R^6)_2$, $NHR^6$, $NR^6C(O)R^5$, or $NO_2$, each of which can be optionally substituted, wherein the backbone of alkyl, alkenyl, or alkynyl optionally comprises one or more heteroatoms, and wherein the carbon to which $R^1$ is attached has the S stereochemistry;

$R^2$ is optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, halogen, CN, $CF_3$, $C(O)R^5$, $CO_2R^5$, $C(O)N(R^6)_2$, $OR^5$, $SR^5$, $SOR^5$, $SO_2R^5$, $OSO_2R^5$, $SSR^5$, $N(R^6)_2$, $NHR^6$, $NR^6C(O)R^5$, or $NO_2$, each of which can be optionally substituted, and wherein the backbone of alkyl, alkenyl, or alkynyl optionally comprises one or more heteroatoms;

$R^3$ is H, optionally substituted linear or branched alkyl, optionally substituted linear or branched alkenyl, optionally substituted linear or branched alkynyl, optionally substituted cyclyl, optionally substituted heterocyclcyl, optionally substituted aryl, or optionally substituted heteroaryl;

$R^4$ is a substituent capable of complexing with a histone deacetylase (HDAC) catalytic site or a metal ion, provided that $R^4$ is not an ester, $CO_2H$, or methyl hydroxamide, $R^5$ is independently for each occurrence H, optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, halogen, CN, $CF_3$, $C(O)R^5$, $CO_2R^5$, $C(O)N(R^6)_2$, $OR^5$, $SR^5$, $SOR^5$, $SO_2R^5$, $SSR^5$, $N(R^6)_2$, $NHR^6$, $NR^6C(O)R^5$, or $NO_2$, each of which can be optionally substituted, wherein the backbone of alkyl, alkenyl, or alkynyl optionally comprises one or more heteroatoms; and R[6] is independently for each occurrence H, optionally substituted linear or branched alkyl, optionally substituted linear or branched alkenyl, optionally substituted linear or branched alkynyl, optionally substituted cyclyl, optionally substituted heterocyclyl, optionally substituted aryl, optionally substituted heteroaryl, halogen, CN, $CF_3$, $C(O)R^5$, $CO_2R^5$, $C(O)N(R^6)_2$, $OR^5$, $SR^5$, $SOR^5$, $SO_2R^5$, $SSR^5$, $N(R^6)_2$, $NHR^6$, $NR^6C(O)R^5$, or $NO_2$, each of which can be optionally substituted, wherein the backbone of alkyl, alkenyl, or alkynyl optionally comprises one or more heteroatoms.

The compounds of formula (I) include pharmaceutically acceptable salts, hydrates, solvates, esters, stereoisomer mixtures, and enantiomers thereof.

The disclosure also provides a pharmaceutical composition comprising a compound of formula (I) and a pharmaceutically acceptable diluent, carrier, or excipient.

In another aspect, the disclosure provides a method of inhibiting histone deacetylase 8 (HDAC-8), the method comprising contacting HDAC-8 with a compound of formula (I). In some embodiments of this, the HDAC-8 is inside a cell. The cell can be a mammalian cell. In some embodiments, the cell is a human cell. In some embodiments, the cell is in vivo.

In yet another aspect, the disclosure provides a method of treating cancer in a subject in need thereof, the method comprising administering to the subject a therapeutically effective amount of a compound of formula (I).

BRIEF DESCRIPTION OF THE DRAWINGS

The patent or application file contains at least one drawing executed in color.

Copies of this patent or patent application publication with color drawing(s) will be provided by the Office upon request and payment of the necessary fee.

DETAILED DESCRIPTION

Figure 1:
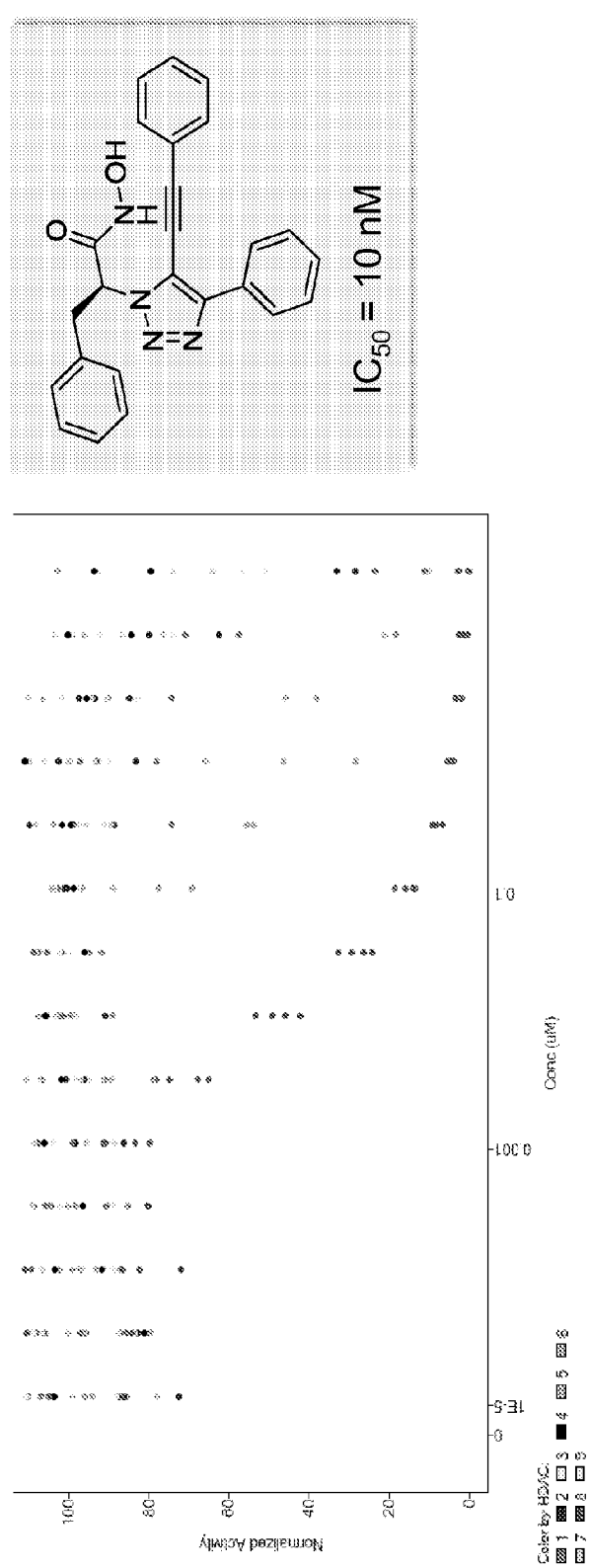
FIG. 1 shows a selective HDAC8 inhibitor according to an embodiment of compounds of formula (I). Also shown is a potential synthesis of compounds of formula (I) from Porco, J. A. Jr. *Tetrahedron* 2006, 62, 6405. It is noted that compounds described in Porco, J. A. Jr. *Tetrahedron* 2006, 62, 6405 are expressly excluded from the compounds of formula (I) described herein.
Figure 1:
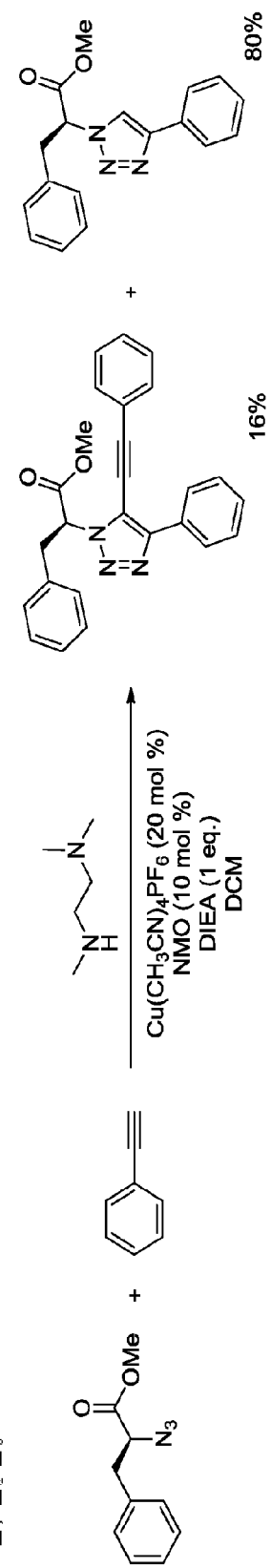

In general, almost all of the inhibitors targeting HDACs are broad spectrum compounds, inhibiting all of the HDAC isoforms with equal potency. These broad spectrum HDAC inhibitors cause the induction of differentiation, growth arrest and/or apoptosis in a large number of tumor cell lines in vitro. Clinical administration of broad spectrum HDAC inhibitors (pan HDAC inhibitors) has been associated with many dose limiting toxicities. These include thrombocytopenia, and other hematological toxicities, QTc prolongation and other cardiac toxicities, nausea, fever, fatigue, and anorexia (For example, see Clinical Cancer Research 2003, 9(10), 3578-3588; Clinical Cancer Research 2002, 8(7), 21422148; and Proceedings of the American Association of Cancer Research 2005, 46, Abs 3978). Selective HDAC inhibitors that selectively inhibit only one HDAC isoform, as opposed to a pan-selective inhibitor, is expected to produce a drug with an improved toxicity profile. Adverse effects in humans have been reported in several clinical trials using pan-HDAC inhibitors. Originally designed for oncological applications, such toxicities might not be crucial when taking into consideration their therapeutic effects and the high mortality rate of cancer.

However, small molecule HDAC inhibitors that are isoform-selective are useful as therapeutic agents with reduced toxicity and as tools for probing the biology of the HDAC isoforms. The present disclosure is based on inventors' discovery of small molecule HDAC inhibitors, which are selective for HDAC8. Accordingly, described herein are selective HDAC8 inhibitor compounds. Compounds described herein selectively inhibit HDAC8 over other HDAC isoforms (e.g. HDACs 1, 2, 3, 6, 10, and 11). HDAC8 is a 377 residue, 42 kDa protein localized to the nucleus of a wide array of tissues, as well as several human tumor cell lines. The wild-type form of full length HDAC8 is described in GenBank Accession Number NP 060956; Buggy, J. J. et al., Biochem. J., 350 (Pt 1), 199-205 (2000). The HDAC8 structure was solved with four different hydroxamate inhibitors bound (Somoza et al., Structure, 2004, 12, 1325)

In one aspect, the present disclosure provides a compound of formula (I):

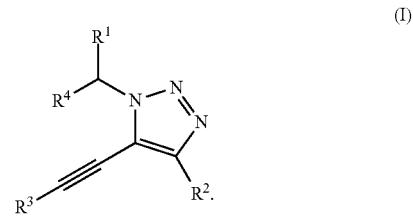

(I)

A skilled artisan recognizes that the carbon atom to which the $R^1$ and $R^4$ substituents are attached can be a chiral center. Therefore, the compound can be in the form of a pure enantiomer. In some embodiments, the carbon to which the $R^1$ and $R^4$ substituents are attached is in the S configuration. In other embodiments, the carbon to which the $R^1$ and $R^4$ substituents are attached is in the R configuration. If the compound of formula (I) comprises more than one chiral center, such compound can be in the form of a single diastereomer.

Substituent $R^1$ can be an selected from linear or branched alkyl, linear or branched alkenyl, linear or branched alkynyl, cyclyl, heterocyclyl, optionally substituted aryl, heteroaryl, halogen, CN, $CF_3$, $C(O)R^5$, $CO_2R^5$, $C(O)N(R^8)_2$, $OR^5$, $SR^5$, $SOR^5$, $SO_2R^5$, $SSR^5N(R^8)_2$, $NHR^8$, $NR^8C(O)R^5$, or $NO_2$, each of which can be optionally substituted, wherein the backbone of alkyl, alkenyl, or alkynyl optionally comprises one or more heteroatoms.

In some embodiments, $R^1$ can be selected from the group consisting of linear or branched $C_1$-$C_{10}$ alkyl, aryl, —$CH_2$-aryl, and —$CH_2$-heteroaryl, each of which can be optionally substituted. In some embodiments, $R^1$ can be selected from benzyl, isopropyl, 1H-indol-3-yl-methyl, and phenyl. In one embodiment, $R^1$ is benzyl.

Substituent $R^2$ can be selected linear or branched alkyl, linear or branched alkenyl, linear or branched alkynyl, cyclyl, heterocyclcyl, optionally substituted aryl, heteroaryl, halogen, CN, $CF_3$, $C(O)R^5$, $CO_2R^5$, $C(O)N(R^6)_2$, $OR^5$, $SR^5$, $SOR^5$, $SO_2R^5$, $SSR^5N(R^6)_2$, $NHR^6$, $NR^6C(O)R^5$, or $NO_2$, each of which can be optionally substituted, wherein the backbone of alkyl, alkenyl, or alkynyl optionally comprises one or more heteroatoms.

In some embodiments, $R^2$ can be selected from the group consisting of linear or branched $C_1$-$C_{10}$ alkyl, cyclyl, heterocyclyl, aryl, and heteroaryl, each of which can be optionally substituted. In some embodiments, $R^2$ is an optionally substituted monocylcylaryl or optionally substituted monocyclylheteroaryl. In one embodiment, $R^2$ is phenyl.

Substituent $R^3$ can be selected from H, optionally substituted linear or branched alkyl, optionally substituted linear or branched alkenyl, optionally substituted linear or branched alkynyl, optionally substituted cyclyl, optionally substituted heterocyclcyl, or optionally substituted aryl, or optionally substituted heteroaryl.

In some embodiments, $R^3$ can be selected from the group consisting of $C_1$-$C_{10}$alkyl, aryl, heteroaryl, cyclyl, heterocyclyl, $C_1$-$C_6$alkyl substituted with 1, 2, or 3 substituents selected from aryl, heteroaryl, cyclyl, heterocyclyl, $OR^5$, $SR^5$, and —$OSO_2R^5$, wherein $R^5$ is alkyl, alkenyl, alkynyl, aryl, heteroaryl, cyclyl, heterocyclyl, and each of which can be optionally substituted.

In some embodiments, $R^3$ is 2-phenyl ethyl, benzenethio methyl, 4-fluoro phenyl, phenoxy methyl, 4-methoxy phenyl, 4-bromo phenyl, 4-t-butyl phenyl, phenyl, 4-cyano phenyl, 2-pyridinyl, 3-pyridinyl, 2-pyranyloxy ethyl, cyclopropyl, isoindoline-1,3-dionyl methyl, 4-phenyl phenyl, 4-ethyl phenyl, cyclopentyl methyl, 3-methoxy phenyl, 4-(N,N-dimethylamino) phenyl, 3-chloro phenyl, 3,5-dimethoxy phenyl, 2,4,5-trimethyl phenyl, 2-methoxy phenyl, 2-methyl-4-methoxyphenyl, 4-acerylamino phenyl, 4-chloro phenyl, 4-methyl-phenylsulfonyloxy methyl, and phenylsulfonyloxy methyl.

In one embodiment, $R^3$ is phenyl or cyclopropyl.

Substituent $R^4$ can be any substituent that is capable of complexing with the histone deacetylase catalytic site or with a metal ion. Zinc ion is known to be present in the catalytic site of HDAC. Accordingly, in some embodiments, the substituent $R^4$ is a substituent that is capable of complexing with a zinc ion. Without wishing to be bound by a theory, the $R^4$ substituent can facilitate binding of the compound of formula (I) to a HDAC by complexing with the zinc ion present in the catalytic site of HDAC. In some embodiments, $R^4$ is not an ester, $CO_2H$, or methyl hydroxyamide.

Examples of substituents capable of complexing with zinc ion that can be used as the $R^4$ substituent include, but are not limited to, —$C(O)R^7$, —NH—$P(O)OR^5$—$R^5$, —$SO_2R^5$, —$SO_2N(R^6)_2$, —$SO_2NR^6OR^5$, or —$SR^5$, wherein $R^7$ is independently for each occurrence H, optionally substituted alkyl, $NR^6OR^5$, amino, —$C(O)N(R^6)_2$, optionally substituted cyclyl, optionally substituted heterocyclyl, optionally substituted aryl, optionally substituted heteroaryl, optionally substituted alkylamino, optionally substituted arylamino, or optionally substituted heteroarylamino.

In some embodiments, $R^7$ can be $NHOR^5$, —$SO_2NHOR^5$, optionally substituted phenylamino, optionally substituted aza-aryl amino, optionally substituted aza-cyclyl, optionally substituted 3-8 membered heterocyclyl, or optionally substituted $C_1$-$C_6$ alkyl. In some embodiments, $R^6$ can be H or optionally substituted $C_1$-$C_{10}$ alkyl. In one embodiment, $R^6$ is H.

In some embodiments, $R^4$ can be —C(O)NHOH, —$CF_3$, —$SO_2NHOH$, —$C(O)CH_2OH$, —$C(O)CH_2SH$, acetyl (—C(O)$CH_3$), —$C(O)CH_2CH_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl.

In one embodiment, $R^4$ is hydroxamic acid, i.e., —C(O)NHOH.

In some embodiments, $R^4$ is not an ester or carboxylic acid, i.e., —C(O)OR, wherein R is H or alkyl. In some embodiments, $R^4$ is not methyl hydroxamide, i.e., —C(O)$NCH_3OH$. In one embodiments, $R^4$ is not —$CO_2H$, —$CO_2CH_3$, —$CO_2CH_2CH_3$, or —$C(O)NCH_3OH$.

Substituent $R^5$ can be selected, independently for each occurrence, from H, optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, wherein the backbone of alkyl, alkenyl, or alkynyl optionally comprises one or more heteroatoms.

In some embodiments, each $R^5$ can be independently H or $C_1$-$C_{10}$alkyl.

Substituent $R^6$ can be selected, independently for each occurrence, from H, linear or branched alkyl, linear or branched alkenyl, linear or branched alkynyl, cyclyl, heterocyclcyl, optionally substituted aryl, heteroaryl, $C(O)R^5$, $CO_2R^5$, $OR^5$, $SR^5$, $SOR^5$, or $SO_2R^5$, each of which can be optionally substituted, and wherein the backbone of alkyl, alkenyl, or alkynyl optionally comprises one or more heteroatoms.

In some embodiments, each $R^6$ can be independently H or $C_1$-$C_{10}$alkyl.

In some embodiments, $R^1$ is linear or branched $C_1$-$C_{10}$ alkyl, aryl, —$CH_2$-aryl, or —$CH_2$-heteroaryl, each of which can be optionally substituted, and $R^2$ is linear or branched $C_1$-$C_{10}$ alkyl, cyclyl, heterocyclyl, aryl, or heteroaryl, each of which can be optionally substituted. In some further embodiments, $R^1$ is benzyl, 2-propyl, 1H-indol-3-yl-methyl, or phenyl, and $R^2$ is an optionally substituted monocylcylaryl or optionally substituted monocyclylheteroaryl. In one embodiment, $R^1$ is benzyl and $R^2$ is phenyl.

In some embodiments, $R^1$ is linear or branched $C_1$-$C_{10}$ alkyl, aryl, —$CH_2$-aryl, or —$CH_2$-heteroaryl, each of which can be optionally substituted, and $R^3$ is $C_1$-$C_{10}$alkyl, aryl, heteroaryl, cyclyl, heterocyclyl, or $C_1$-$C_6$alkyl substituted with 1, 2, or 3 substituents selected from aryl, heteroaryl, cyclyl, heterocyclyl, $OR^5$, $SR^5$, or —$OSO_2R^5$. In some further embodiments of this, $R^1$ is benzyl, 2-propyl, 1H-indol-3-yl-methyl, phenyl, or indol-3-yl-methyl, and $R^3$ is 2-phenyl ethyl, benzenethio methyl, 4-fluoro phenyl, phenoxy methyl, 4-methoxy phenyl, 4-bromo phenyl, 4-t-butyl phenyl, phenyl, 4-cyano phenyl, 2-pyridinyl, 3-pyridinyl, 2-pyranyloxy ethyl, cyclopropyl, isoindoline-1,3-dionyl methyl, 4-phenyl phenyl, 4-ethyl phenyl, cyclopentyl methyl, 3-methoxy phenyl, 4-(N,N-dimethylamino) phenyl, 3-chloro phenyl, 3,5-dimethoxy phenyl, 2,4,5-trimethyl phenyl, 2-methoxy phenyl, 2-methyl-4-methoxyphenyl, 4-acerylamino phenyl, 4-chloro phenyl, 4-methyl-phenylsulfonyloxy methyl, or phenylsulfonyloxy methyl. In one embodiment, $R^1$ is benzyl and $R^3$ is phenyl or cyclopropyl.

In some embodiments, $R^1$ is linear or branched $C_1$-$C_{10}$ alkyl, aryl, —$CH_2$-aryl, or —$CH_2$-heteroaryl, each of which can be optionally substituted, and $R^4$ is —C(O)$R^7$, —NH—P(O)O$R^5$—$R^5$, —SO$_2$$R^5$, —SO$_2$N($R^8$)$_2$, —SO$_2$N$R^8$O$R^5$, or —S$R^5$. In some further embodiments, $R^1$ is benzyl, 2-propyl, 1H-indol-3-yl-methyl, phenyl, or indol-3-yl-methyl, and $R^4$ is —C(O)NHOH, —CF$_3$, —SO$_2$NHOH, —C(O)CH$_2$OH, —C(O)CH$_2$SH, acetyl (—C(O)CH$_3$), —C(O)CH$_2$CH$_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl. In one embodiment, $R^1$ is benzyl and $R^4$ is hydroxamic acid, i.e., —C(O)NHOH.

In some embodiments, $R^2$ is linear or branched $C_1$-$C_{10}$ alkyl, cyclyl, heterocyclyl, aryl, or heteroaryl, each of which can be optionally substituted, and $R^3$ is $C_1$-$C_{10}$alkyl, aryl, heteroaryl, cyclyl, heterocyclyl, or $C_1$-$C_6$alkyl substituted with 1, 2, or 3 substituents selected from aryl, heteroaryl, cyclyl, heterocyclyl, O$R^5$, S$R^5$, or —OSO$_2$$R^5$. In some further embodiments, $R^2$ is an optionally substituted monocylcylaryl or optionally substituted monocyclylheteroaryl and $R^3$ is 2-phenyl ethyl, benzenethio methyl, 4-fluoro phenyl, phenoxy methyl, 4-methoxy phenyl, 4-bromo phenyl, 4-t-butyl phenyl, phenyl, 4-cyano phenyl, 2-pyridinyl, 3-pyridinyl, 2-pyranyloxy ethyl, cyclopropyl, isoindoline-1,3-dionyl methyl, 4-phenyl phenyl, 4-ethyl phenyl, cyclopentyl methyl, 3-methoxy phenyl, 4-(N,N-dimethylamino) phenyl, 3-chloro phenyl, 3,5-dimethoxy phenyl, 2,4,5-trimethyl phenyl, 2-methoxy phenyl, 2-methyl-4-methoxyphenyl, 4-acerylamino phenyl, 4-chloro phenyl, 4-methyl-phenylsulfonyloxy methyl, or phenylsulfonyloxy methyl. In one embodiment, $R^2$ is phenyl and $R^3$ is phenyl or cyclopropyl.

In some embodiments, $R^2$ is linear or branched $C_1$-$C_{10}$ alkyl, cyclyl, heterocyclyl, aryl, or heteroaryl, each of which can be optionally substituted, and $R^4$ is —C(O)$R^7$, —NH—P(O)O$R^5$—$R^5$, —SO$_2$$R^5$, —SO$_2$N($R^8$)$_2$, —SO$_2$N$R^8$O$R^5$, or —S$R^5$. In some further embodiments, $R^2$ is an optionally substituted monocylcylaryl or optionally substituted monocyclylheteroaryl and $R^4$ is —C(O)NHOH, —CF$_3$, —SO$_2$NHOH, —C(O)CH$_2$OH, —C(O)CH$_2$SH, acetyl (—C(O)CH$_3$), —C(O)CH$_2$CH$_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl. In one embodiment, $R^2$ is phenyl and $R^4$ is hydroxamic acid (—C(O)NHOH).

In some embodiments, $R^3$ is $C_1$-$C_{10}$alkyl, aryl, heteroaryl, cyclyl, heterocyclyl, or $C_1$-$C_6$alkyl substituted with 1, 2, or 3 substituents selected from aryl, heteroaryl, cyclyl, heterocyclyl, O$R^5$, S$R^5$, and —OSO$_2$$R^5$, and $R^4$ is —C(O)$R^7$, —NH—P(O)O$R^5$—$R^5$, —SO$_2$$R^5$, —SO$_2$N($R^6$)$_2$, —SO$_2$N$R^6$O$R^5$, or —S$R^5$. In some further embodiments, $R^3$ is 2-phenyl ethyl, benzenethio methyl, 4-fluoro phenyl, phenoxy methyl, 4-methoxy phenyl, 4-bromo phenyl, 4-t-butyl phenyl, phenyl, 4-cyano phenyl, 2-pyridinyl, 3-pyridinyl, 2-pyranyloxy ethyl, cyclopropyl, isoindoline-1,3-dionyl methyl, 4-phenyl phenyl, 4-ethyl phenyl, cyclopentyl methyl, 3-methoxy phenyl, 4-(N,N-dimethylamino) phenyl, 3-chloro phenyl, 3,5-dimethoxy phenyl, 2,4,5-trimethyl phenyl, 2-methoxy phenyl, 2-methyl-4-methoxyphenyl, 4-acerylamino phenyl, 4-chloro phenyl, 4-methyl-phenylsulfonyloxy methyl, or phenylsulfonyloxy methyl, and $R^4$ is —C(O)NHOH, —CF$_3$, —SO$_2$NHOH, —C(O)CH$_2$OH, —C(O)CH$_2$SH, acetyl (—C(O)CH$_3$), —C(O)CH$_2$CH$_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl. In one embodiment, $R^3$ is phenyl or cyclopropyl and $R^4$ is hydroxamic acid (—C(O)NHOH).

In some embodiments, $R^1$ is linear or branched $C_1$-$C_{10}$ alkyl, aryl, —CH$_2$-aryl, or —CH$_2$-heteroaryl, each of which can be optionally substituted, and $R^2$ is linear or branched $C_1$-$C_{10}$ alkyl, cyclyl, heterocyclyl, aryl, or heteroaryl, each of which can be optionally substituted, and $R^4$ is —C(O)$R^7$, —NH—P(O)O$R^5$—$R^5$, —SO$_2$$R^5$, —SO$_2$N($R^6$)$_2$, —SO$_2$N$R^6$O$R^5$, or —S$R^5$. In some further embodiments of this, $R^1$ is benzyl, 2-propyl, 1H-indol-3-yl-methyl, phenyl, or indol-3-yl-methyl, and $R^2$ is an optionally substituted monocylcylaryl or optionally substituted monocyclylheteroaryl, and $R^4$ is C(O)NHOH, —CF$_3$, —SO$_2$NHOH, —C(O)CH$_2$OH, —C(O)CH$_2$SH, acetyl (—C(O)CH$_3$), —C(O)CH$_2$CH$_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl. In one embodiment, $R^1$ is benzyl, $R^2$ is phenyl and $R^4$ is hydroxamic acid (—C(O)NHOH).

In some embodiments, $R^1$ is linear or branched $C_1$-$C_{10}$ alkyl, aryl, —CH$_2$-aryl, or —CH$_2$-heteroaryl, each of which can be optionally substituted, and $R^3$ is $C_1$-$C_{10}$alkyl, aryl, heteroaryl, cyclyl, heterocyclyl, or $C_1$-$C_6$alkyl substituted with 1, 2, or 3 substituents selected from aryl, heteroaryl, cyclyl, heterocyclyl, O$R^5$, S$R^5$, and —OSO$_2$$R^5$, and $R^4$ is —C(O)$R^7$, —NH—P(O)O$R^5$—$R^5$, —SO$_2$$R^5$, —SO$_2$N($R^6$)$_2$, —SO$_2$N$R^6$O$R^5$, or —S$R^5$. In some further embodiments of this, $R^1$ is benzyl, 2-propyl, 1H-indol-3-yl-methyl, phenyl, or indol-3-yl-methyl, and $R^3$ 2-phenyl ethyl, benzenethio methyl, 4-fluoro phenyl, phenoxy methyl, 4-methoxy phenyl, 4-bromo phenyl, 4-t-butyl phenyl, phenyl, 4-cyano phenyl, 2-pyridinyl, 3-pyridinyl, 2-pyranyloxy ethyl, cyclopropyl, isoindoline-1,3-dionyl methyl, 4-phenyl phenyl, 4-ethyl phenyl, cyclopentyl methyl, 3-methoxy phenyl, 4-(N,N-dimethylamino) phenyl, 3-chloro phenyl, 3,5-dimethoxy phenyl, 2,4,5-trimethyl phenyl, 2-methoxy phenyl, 2-methyl-4-methoxyphenyl, 4-acerylamino phenyl, 4-chloro phenyl, 4-methyl-phenylsulfonyloxy methyl, or phenylsulfonyloxy methyl, and $R^4$ is C(O)NHOH, —CF$_3$, —SO$_2$NHOH, —C(O)CH$_2$OH, —C(O)CH$_2$SH, acetyl (—C(O)CH$_3$), —C(O)CH$_2$CH$_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl. In one embodiment, $R^1$ is benzyl, $R^3$ is phenyl or cyclopropyl, and $R^4$ is hydroxamic acid (—C(O)NHOH).

In some embodiments, $R^2$ is linear or branched $C_1$-$C_{10}$ alkyl, cyclyl, heterocyclyl, aryl, or heteroaryl, each of which can be optionally substituted, and $R^3$ is $C_1$-$C_{10}$alkyl, aryl, heteroaryl, cyclyl, heterocyclyl, or $C_1$-$C_6$alkyl substituted with 1, 2, or 3 substituents selected from aryl, heteroaryl, cyclyl, heterocyclyl, O$R^5$, S$R^5$, and —OSO$_2$$R^5$, and $R^4$ is —C(O)$R^7$, —NH—P(O)O$R^5$—$R^5$, —SO$_2$$R^5$, —SO$_2$N($R^6$)$_2$, —SO$_2$N$R^6$O$R^5$, or —S$R^5$. In some further embodiments of this, $R^2$ is an optionally substituted monocylcylaryl or optionally substituted monocyclylheteroaryl, and $R^3$ 2-phenyl ethyl, benzenethio methyl, 4-fluoro phenyl, phenoxy methyl, 4-methoxy phenyl, 4-bromo phenyl, 4-t-butyl phenyl, phenyl, 4-cyano phenyl, 2-pyridinyl, 3-pyridinyl, 2-pyranyloxy ethyl, cyclopropyl, isoindoline-1,3-dionyl methyl, 4-phenyl phenyl, 4-ethyl phenyl, cyclopentyl methyl, 3-methoxy phenyl, 4-(N,N-dimethylamino) phenyl, 3-chloro phenyl, 3,5-dimethoxy phenyl, 2,4,5-trimethyl phenyl, 2-methoxy phenyl, 2-methyl-4-methoxyphenyl, 4-acerylamino phenyl, 4-chloro phenyl, 4-methyl-phenylsulfonyloxy methyl, or phenylsulfonyloxy methyl, and $R^4$ is C(O)NHOH, —$CF_3$, —$SO_2$NHOH, —C(O)$CH_2$OH, —C(O)$CH_2$SH, acetyl (—C(O)$CH_3$), —C(O)$CH_2CH_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl. In one embodiment, $R^2$ is phenyl, $R^3$ is phenyl or cyclopropyl, and $R^4$ is hydroxamic acid (—C(O)NHOH).

In some embodiments, $R^1$ is linear or branched $C_1$-$C_{10}$ alkyl, aryl, —$CH_2$-aryl, or —$CH_2$-heteroaryl, each of which can be optionally substituted, and $R^2$ is linear or branched $C_1$-$C_{10}$ alkyl, cyclyl, heterocyclyl, aryl, or heteroaryl, each of which can be optionally substituted, and $R^3$ is $C_1$-$C_{10}$alkyl, aryl, heteroaryl, cyclyl, heterocyclyl, or $C_1$-$C_6$alkyl substituted with 1, 2, or 3 substituents selected from aryl, heteroaryl, cyclyl, heterocyclyl, $OR^5$, $SR^5$, and —$OSO_2R^5$, and $R^4$ is —C(O)$R^7$, —NH—P(O)$OR^5$—$R^5$, —$SO_2R^5$, —$SO_2N(R^6)_2$, —$SO_2NR^6OR^5$, or —$SR^5$. In some further embodiments of this, $R^1$ is benzyl, 2-propyl, 1H-indol-3-yl-methyl, phenyl, or indol-3-yl-methyl, and $R^2$ is an optionally substituted monoclyclaryl or optionally substituted monocyclylheteroaryl, and $R^3$ 2-phenyl ethyl, benzenethio methyl, 4-fluoro phenyl, phenoxy methyl, 4-methoxy phenyl, 4-bromo phenyl, 4-t-butyl phenyl, phenyl, 4-cyano phenyl, 2-pyridinyl, 3-pyridinyl, 2-pyranyloxy ethyl, cyclopropyl, isoindoline-1,3-dionyl methyl, 4-phenyl phenyl, 4-ethyl phenyl, cyclopentyl methyl, 3-methoxy phenyl, 4-(N,N-dimethylamino) phenyl, 3-chloro phenyl, 3,5-dimethoxy phenyl, 2,4,5-trimethyl phenyl, 2-methoxy phenyl, 2-methyl-4-methoxyphenyl, 4-acerylamino phenyl, 4-chloro phenyl, 4-methyl-phenylsulfonyloxy methyl, or phenylsulfonyloxy methyl, and $R^4$ is C(O)NHOH, —$CF_3$, —$SO_2$NHOH, —C(O)$CH_2$OH, —C(O)$CH_2$SH, acetyl (—C(O)$CH_3$), —C(O)$CH_2CH_3$, 2-amino-phenylamino-carbonyl, 2-hydroxy-phenylamino-carbonyl, thiazolyl-amino carbonyl, oxazolylamino carbonyl, 4,5-dihydro-oxazolylamino carbonyl, or oxiranyl carbonyl. In one embodiment, $R^1$ is benzyl, R2 is phenyl, $R^3$ is phenyl or cyclopropyl, and $R^4$ is hydroxamic acid (—C(O)NHOH).

In some embodiments, a compound of formula (I) has the structure shown in formula (IA):

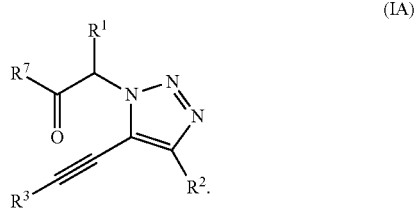

(IA)

wherein $R^1$, $R^2$, $R^3$ and $R^7$ are as described herein for formula (I).

Figure 3:
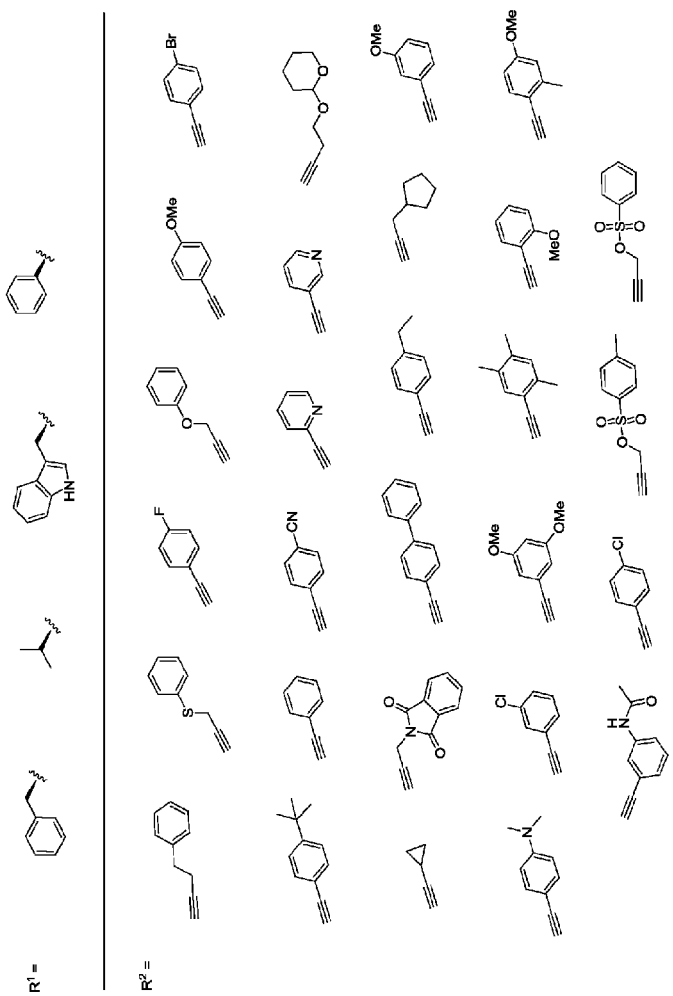
FIG. 3 shows some exemplary compounds of formula (I). It is to be noted that the structures shown for $R^2$ are connected to the rest of the compound via the terminal carbon of the alkyne, i.e., the alkyne hydrogen is replaced by the rest of the compound structure.
Figure 4:
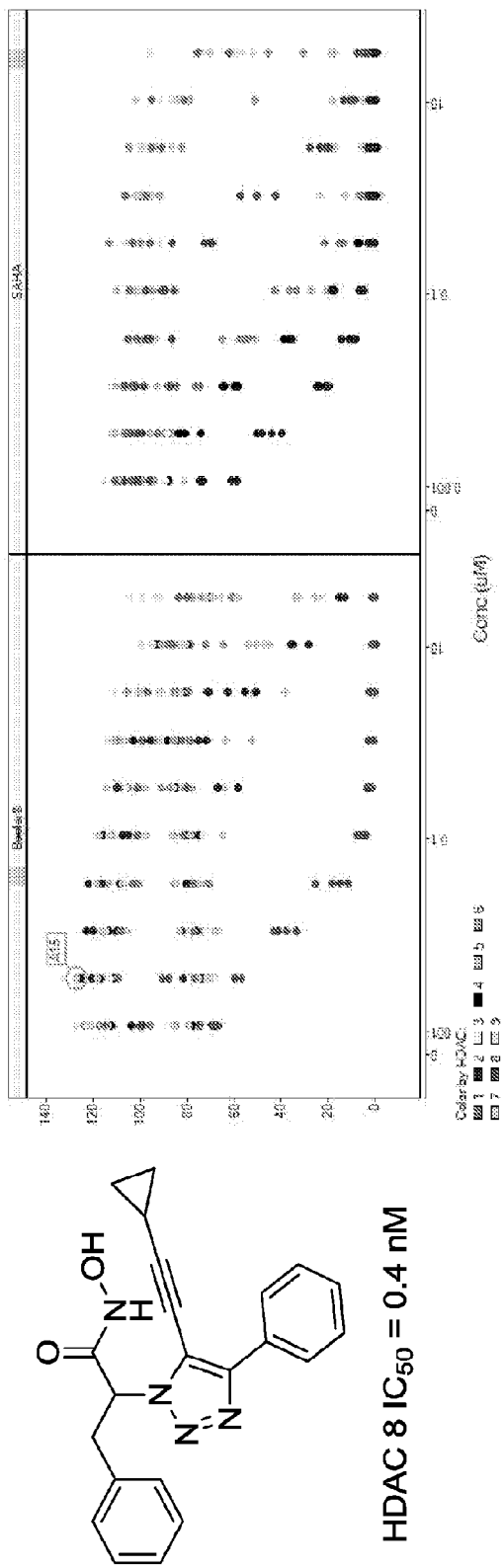
FIG. 4 shows that a compound of formula (I) having a cyclopropyl as the $R^3$ substituent is a potent and selective HDAC8 inhibitor available.
Figure 5:
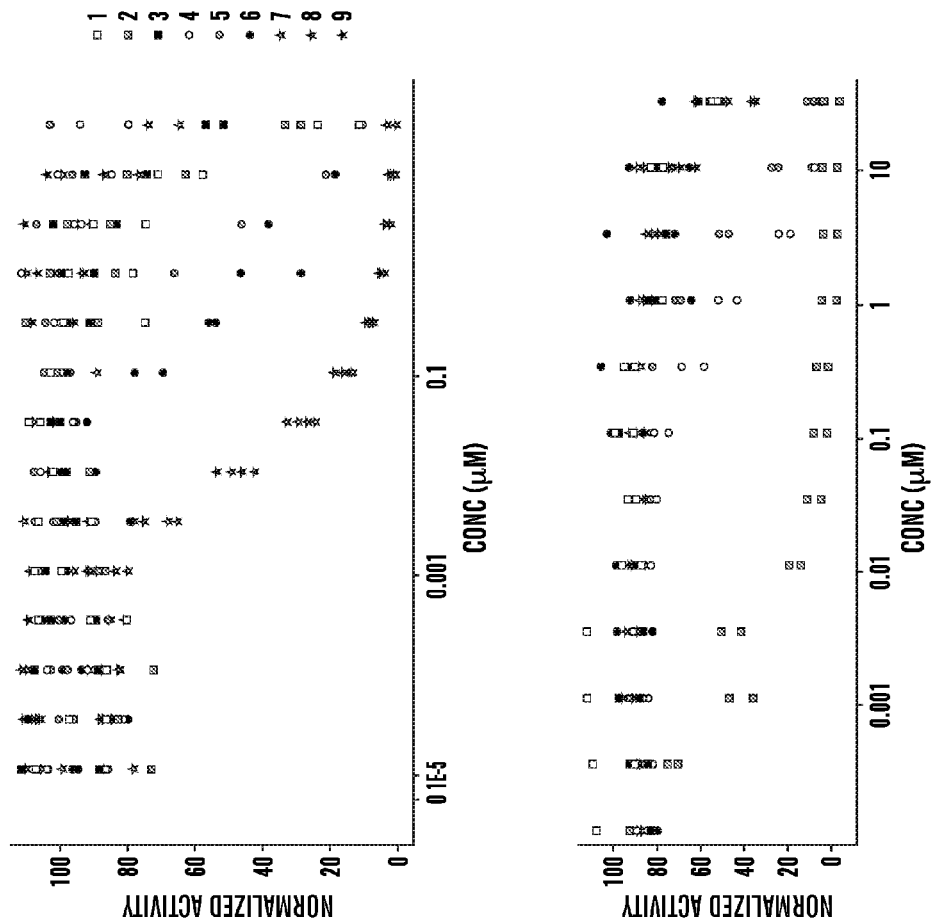
FIG. 5 shows structures and HDAC activity of two compounds according to embodiments of formula (I).
Figure 5:
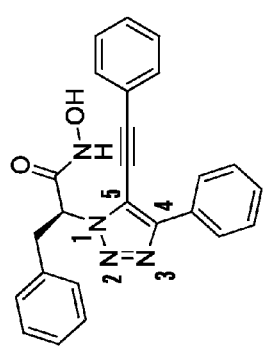
Figure 5:
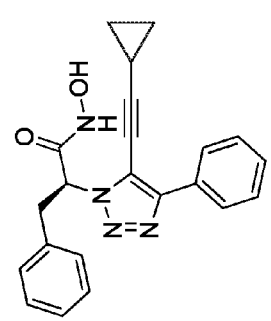
Figure 6:
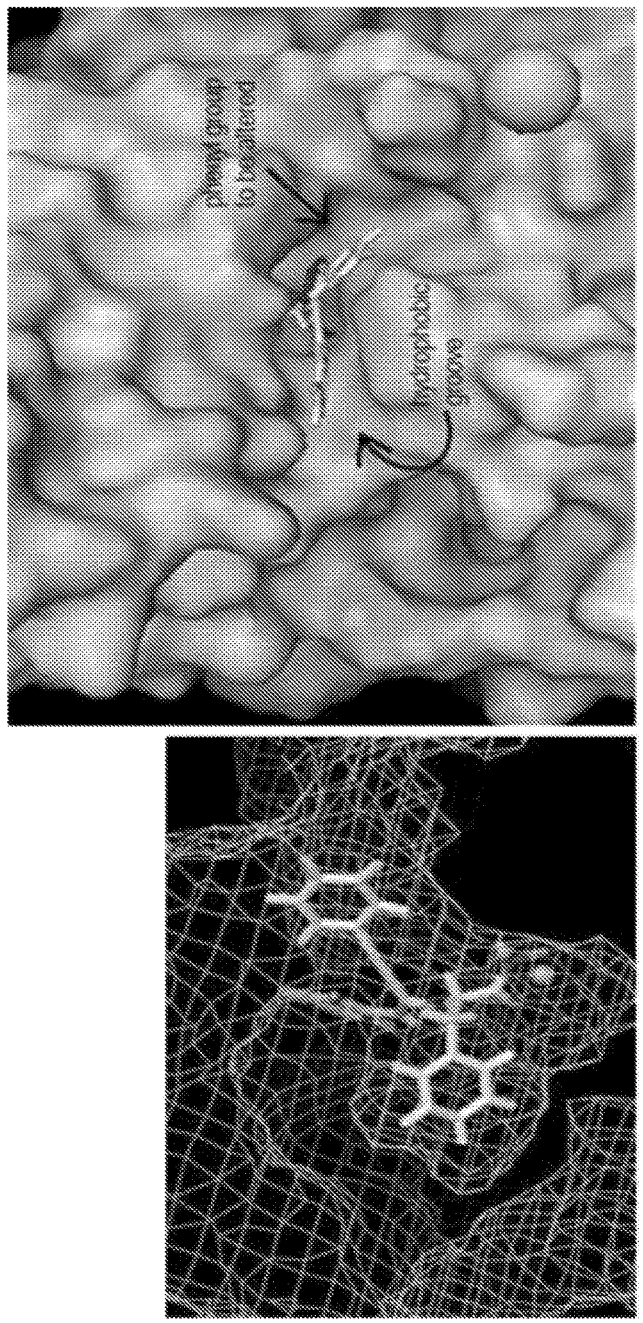
FIG. 6 shows results of molecular modeling of a compound of formula (I) with the binding pocket of HDAC 8. As seen the phenyl group from the original amino methyl ester fits snuggly into the Zn binding site and the alkynyl phenyl group sits flat in a hydrophobic groove.

In some embodiments, the compound of formula (I) is selected from those shown in FIG. 3, e.g., a compound of formula (IB),

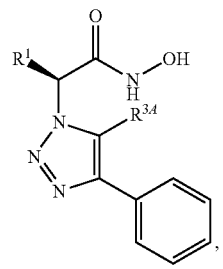

wherein $R^1$ is benzyl, 2-propyl, 1H-indol-3-yl-methyl, or phenyl; and $R^{3A}$ is selected from

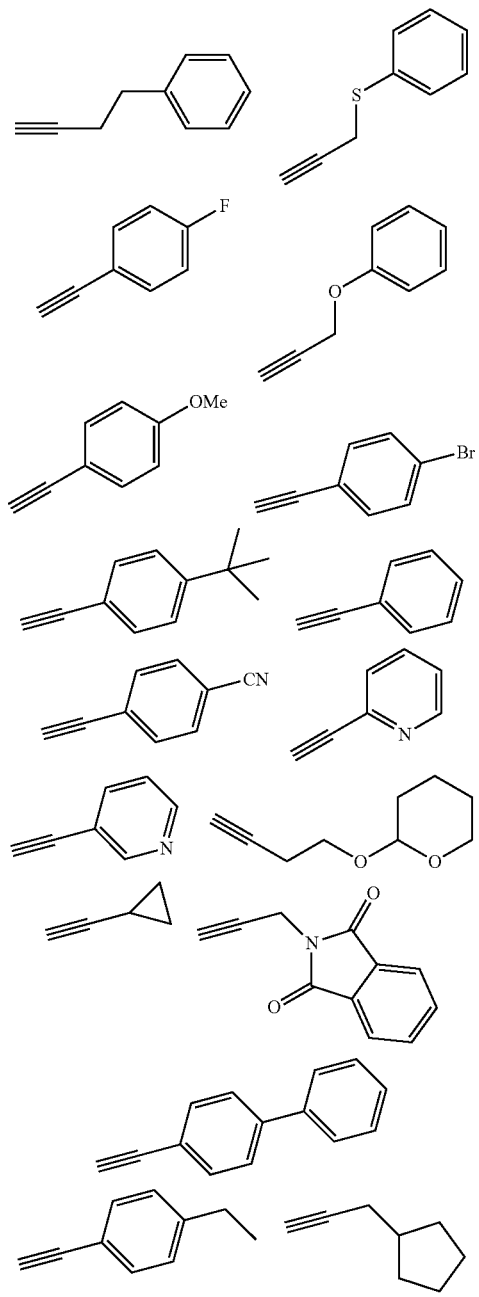

-continued

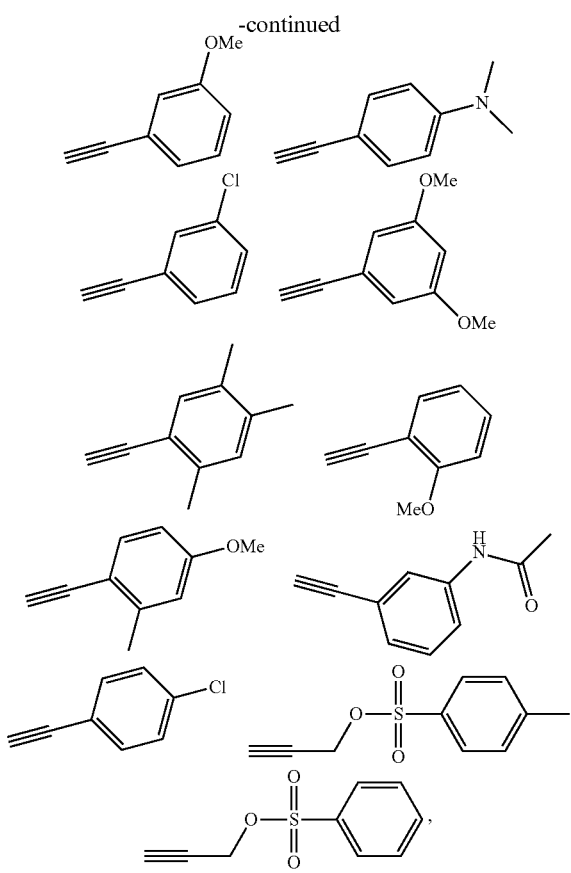

wherein R³ᴬ is connected via the carbon on the terminal end of the alkyne shown in the structures.

In some embodiments, the compound of formula (I) is

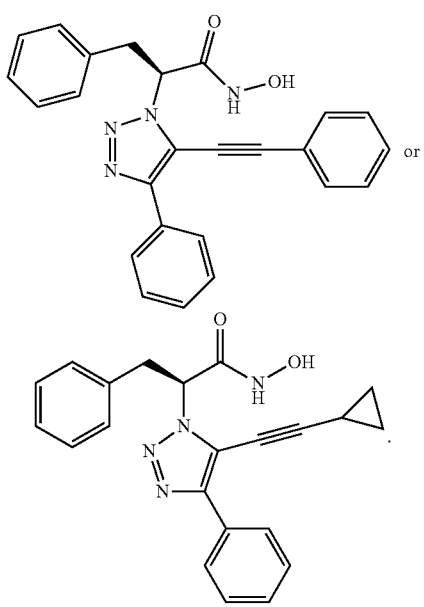

In some embodiments, the compound of formula (I) does not include a compound wherein: (i) R¹ is benzyl, R² is phenyl, R³ is phenyl, and R⁴ is —CO₂CH₃; (ii) R¹ is benzyl, R² is phenoxymethyl, R³ is phenoxymethyl, and R⁴ is —CO₂CH₂CH₃; (iii) R¹ is methyl, R² is phenoxymethyl, R³ is phenoxymethyl, and R⁴ is

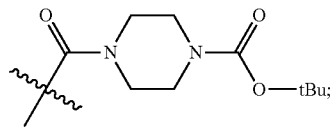 [SMILES: *C(=O)N1CCN(C(=O)OC(C)(C)C)CC1]

(iv) R¹ is benzyl, R² is 1-propyl, R³ is 1-propyl, and R⁴ is —CO₂CH₃; or (v) R¹ is benzyl, R² is methoxymethyl, R³ is methoxymethyl, and R⁴ is —CO₂CH₃.

The following compounds, described in Porco, J. A. Jr. *Tetrahedron* 2006, 62, 6405, are expressly excluded from the novel compounds of Formula (I):

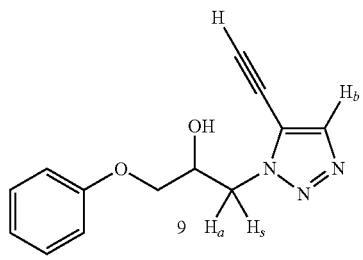

(1-(5-ethynyl-[1,2,3]triazol-1-yl)-3-phenoxy-propan-2-ol);

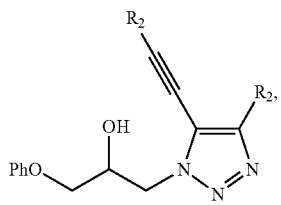

wherein both R₂ are CH₂OMe (1-[4-Methoxymethyl-5-(3-methoxy-prop-1-ynyl)-[1,2,3]-triazol-1-yl]-3-phenoxy-propan-2-ol) or both R₂ are propyl(1-(5-Pent-1-ynyl-4-propyl-[1,2,3]-triazol-1-yl)-3-phenoxy-propan-2-ol);

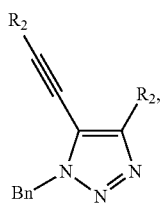

wherein both R₂ are propyl(1-Benzyl-4-methoxymethyl-5-(3-methoxy-prop-1-ynyl)-1H-[1,2,3]-triazole) or both R₂ are phenyl(1-Benzyl-5-pent-1-ynyl-4-propyl-1H-[1,2,3]-triazole);

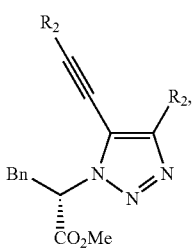

wherein both $R_2$ are $CH_2OMe$ (2-[4-Methoxymethyl-5-(3-methoxy-prop-1-ynyl)-[1,2,3]-triazol-1-yl]-3-phenyl-propionic acid methyl ester) or both $R_2$ are propyl(2-(5-Pent-1-ynyl-4-propyl-[1,2,3]-triazol-1-yl)-3-phenyl-propionic acid methyl ester);

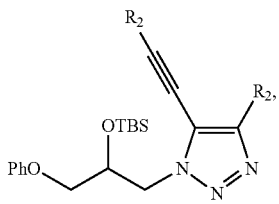

wherein both $R_2$ are $CH_2OMe$ (1-[2-(tert-Butyl-dimethyl-silanyloxy)-3-phenoxy-propyl]-4-methoxymethyl-5-(3-methoxy-prop-1-ynyl)-1H-[1,2,3]-triazole); and

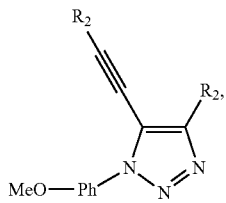

wherein both $R_2$ are $CH_2OMe$ (4-Methoxymethyl-5-(3-methoxy-prop-1-ynyl)-1-(4-methoxy-phenyl)-1H-[1,2,3]-triazole).

It should be recognized that the compounds described herein can be present and optionally administered in the form of salts, hydrates and prodrugs that are converted in vivo into the compounds described herein. For example, it is within the scope of the present invention to convert the compounds described herein into and use them in the form of their pharmaceutically acceptable salts derived from various organic and inorganic acids and bases in accordance with procedures well known in the art.

When the compounds described herein possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts amenable to the disclosed compounds include, but are not limited to, adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (frommucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds described herein possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts amenable to the disclosed compounds include, but are not limited to, copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine(tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups can be quaternized with such agents as $C_1$-$C_4$alkyl halides, e.g., methyl, ethyl, isopropyl and tert-butyl chlorides, bromides and iodides; di($C_1$-$C_4$alkyl) sulfates, e.g., dimethyl, diethyl and diamyl sulfates; $C_{10}$-$C_{18}$alkyl halides, e.g., decyl, dodecyl, lauryl, myristyl and stearyl chlorides, bromides and iodides; and aryl($C_1$-$C_4$alkyl) halides, e.g., benzyl chloride and phenethyl bromide. Such salts permit the preparation of both water-soluble and oil-soluble compounds described herein.

Prodrug derivatives of compounds described herein can be prepared by modifying substituents of compounds described herein that are then converted in vivo to a different substituent. It is noted that in many instances, the prodrugs themselves also fall within the scope of the range of compounds described herein. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al., 1994, *Bioorganic and Medicinal Chemistry Letters*, Vol. 4, p. 1985.

Protected derivatives of compounds described herein can also be made. Examples of techniques applicable to the creation of protecting groups and their removal can be found in T. W. Greene, *Protecting Groups in Organic Synthesis*, 4th edition, John Wiley & Sons, Inc. 2006.

Compounds described herein can also be conveniently prepared or formed during the process of the invention, as solvates (e.g. hydrates). Hydrates of the compounds described herein can be conveniently prepared by recrystallization from an aqueous/organic solvent mixture, using organic solvents such as dioxin, tetrahydrofuran or methanol.

In some embodiments, the compounds of the present disclosure can be used in the form of a pharmaceutically acceptable salt. A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-methylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibenzylethylenediamine, and the like), and optionally substituted ethanol-amines (e.g., ethanolamine, diethanolamine, triethanolamine and the like), Preparation of Compounds The compounds according to the disclosure can be prepared by synthetic processes which are known to those skilled in the art, particularly in view of the state of the art and the specific preparatory examples provided below herein. Suitable modification to starting materials by methods well known in the art may also be employed. Representative methods for synthesizing these compounds are provided in the Examples. It is noted, however, that the compounds described herein can also be synthesized by other synthetic routes that others may devise.

It will be readily recognized that certain compounds described herein have atoms with linkages to other atoms that confer a particular stereochemistry to the compound (e.g., chiral centers). It is recognized that synthesis of compounds according to the present invention can result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

In one aspect provided herein is method of preparing a compound of formula (II). Generally the method comprises (i) reacting a compound of formula (III) and IV) to obtain a compound of formula (V); and reacting the compound of formula (V) from step (i) with a compound of formula (VI) to obtain the compound of formula (II),

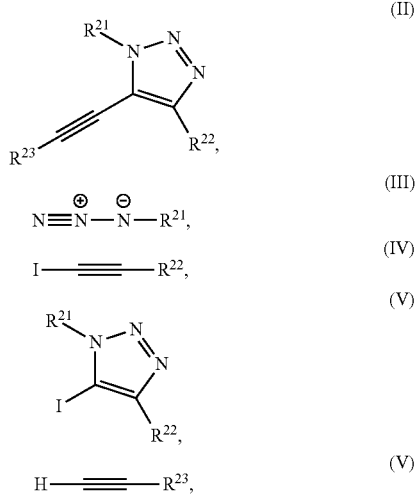

wherein: $R^{21}$ is H or —$CHR^1R^4$; $R^{22}$ is H or —$R^2$; $R^{23}$ is H or —$R^3$; and $R^1$, $R^2$, $R^3$ and $R^4$ are as defined for formula (I).

In one embodiment of the method, $R^{21}$ is —$CHR^1R^4$, $R^{22}$ is $R^2$, and $R^{23}$ is $R^3$, wherein $R^1$, $R^2$, $R^3$, and $R^4$ are as described herein for compounds of formula (I).

Compounds described herein, pharmaceutically acceptable salts, pharmaceutically acceptable N-oxides, pharmaceutically active metabolites, pharmaceutically acceptable prodrugs, or pharmaceutically acceptable solvates thereof, inhibit HDAC8 activity, and are used to treat patients where inhibition of HDAC8 activity provides benefit. Compounds described herein are selective HDAC8 inhibitor compounds.

A "selective HDAC8 inhibitor," as used herein, refers to a compound that has an $IC_{50}$ for inhibition of HDAC8 deacetylase activity that is at least about 5 fold to more than about 500 fold lower than the IC50 for inhibition of deacetylase activity of another HDAC. In some embodiments, the selective HDAC8 inhibitor has an $IC_{50}$ for inhibition of HDAC8 deacetylase activity that is about 5, about 10, about 50, about 100, about 150, about 200, about 250, about 300, about 350, about 400, about 450 or more than about 500 fold lower than the $IC_{50}$ for inhibition of deacetylase activity of another HDAC. In one embodiment, the selective HDAC8 inhibitor has an $IC_{50}$ for inhibition of HDAC8 deacetylase activity that is at least about 10 fold lower than the $IC_{50}$ for inhibition of deacetylase activity of at least one of HDAC 1, HDAC2, HDAC3, HDAC6, HDAC10, and HDAC11; in another embodiment at least two of HDAC1, HDAC2, HDAC3, HDAC6, HDAC10, and HDAC11; in another embodiment all of HDAC1, HDAC2, HDAC3, HDAC6, HDAC10, and HDAC11. In another embodiment, the selective HDAC8 inhibitor has an $IC_{50}$ for HDAC8 deacetylase activity that is at least about 20 fold lower than the IC50 for inhibition of deacetylase activity of at least one of HDAC 1, HDAC2, HDAC3, HDAC6, HDAC10, and HDAC11; in another embodiment at least two of HDAC1, HDAC2, HDAC3, HDAC6, HDAC10, and HDAC11; in another embodiment all of HDAC1, HDAC2, HDAC3, HDAC6, HDAC10, and HDAC11.

In some embodiments of the methods described herein, the selective HDAC8 inhibitor has an $IC_{50}$ for HDAC8 that is at least about 10 fold lower than the $IC_{50}$ for HDAC1, HDAC2, HDAC3, HDAC6, HDAC10, or HDAC11. In some embodiments of any of the methods described herein, the selective HDAC8 inhibitor has an $IC_{50}$ for HDAC8 that is less than about 100 nM and that is at least about 10 fold lower than the $IC_{50}$ for HDAC1, HDAC2, HDAC3, HDAC6, HDAC10, or HDAC11. In some embodiments of any of the methods described herein, the selective HDAC8 inhibitor has an $IC_{50}$ for HDAC8 that is less than about 50 nM and that is at least about 10 fold lower than the $IC_{50}$ of the selective inhibitor for HDAC1, HDAC2, HDAC3, HDAC6, HDAC10, or HDAC11.

In some embodiments, selective HDAC8 inhibitors described herein have an $IC_{50}$ for HDAC8 that is at least about 15 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least about 20 fold lower than the $IC_{50}$ for HDAC1, HDAC2, HDAC3, HDAC6, and HDAC10. In some embodiments, selective HDAC8 inhibitors described herein have an $IC_{50}$ for HDAC8 that is at least about 100 fold lower than the $IC_{50}$ for HDAC1, HDAC2, HDAC3, HDAC6, and HDAC10. In addition, selective HDAC8 inhibitors described herein have an $IC_{50}$ for HDAC8 that is less than about 100 nM while the $IC_{50}$ for HDAC1, HDAC2, HDAC3, HDAC6, and HDAC10 is greater than about 100 nM.

In some embodiments, selective HDAC8 inhibitors described herein have an $IC_{50}$ for HDAC8 that is at least about 10 fold lower than the $IC_{50}$ for HDAC1. In some embodiments, selective HDAC8 inhibitors described herein have an $IC_{50}$ for HDAC8 that is at least about 20 fold lower than the $IC_{50}$ for HDAC1. In some embodiments, selective HDAC8 inhibitors described herein have an $IC_{50}$ for HDAC8 that is at least about 40 fold lower than the $IC_{50}$ for HDAC1. In some embodiments, selective HDAC8 inhibitors described herein have an $IC_{50}$ for HDAC8 that is at least about 100 fold lower than the $IC_{50}$ for HDAC1. In some embodiments, selective HDAC8 inhibitors described herein have an $IC_{50}$ for HDAC8 that is at least about 150 fold lower than the $IC_{50}$ for HDAC1. In yet other embodiments, selective HDAC8 inhibitors described herein have an IC50 for HDAC8 that is at least about 200 fold lower than the $IC_{50}$ for HDAC1.

In some embodiments, selective HDAC8 inhibitors described herein have $IC_{50}$ for HDAC8 that is less than about 100 nM and that is at least about 20 fold lower than the $IC_{50}$ for other HDAC isoforms (HDAC1, HDAC2, HDAC3, HDAC6, HDAC10), wherein the $IC_{50}$ for the other HDAC isoforms is greater than about 100 nM.

The compounds described herein can be tested for activity against one or more HDACs as described in U.S. Patent Publication No. 2005/0159470, content of which is incorporated by reference in its entirety.

Methods

In another aspect, described herein is a method of inhibiting an HDAC, e.g., HDAC8, the method comprising contacting the HDAC with a compound described herein. As used herein, the term "inhibit," with reference to the HDAC activity, means to regulate negatively the normal functioning of the HDAC. In some embodiments, a compound described herein can reduce the activity of the HDAC by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to a reference or a control. In some embodiments, the compound described herein completely inhibits the activity of the HDAC, i.e., 100% inhibition. In some other embodiments, the compound described herein does not completely inhibits the activity of the HDAC, i.e., less than 100% inhibition.

The HDAC can be present either inside or outside a cell. When the HDAC is present in a cell the cell can be contacted with the compound in a cell culture e.g., in vitro or ex vivo, or the compound can be administered to a subject, e.g., in vivo. The term "contacting" or "contact" as used herein in connection with contacting a cell includes subjecting the cell to an appropriate culture media which comprises the indicated compound. Where the cell is in vivo, "contacting" or "contact" includes administering the compound in a pharmaceutical composition to a subject via an appropriate administration route such that the compound contacts the cell in vivo. For in vivo methods, a therapeutically effective amount of a compound can be administered to a subject. Methods of administering compounds to a subject are known in the art and easily available to one of skill in the art.

Without limitations, the cell can be from any source desirable. For example, the cell can from a mammal. In some embodiments, the cell is a human cell. In some embodiments, the cell is a cancer cell. As used herein, the term "cancer cell" refers to a cell undergoing early, intermediate or advanced stages of multi-step neoplastic progression as described, for example, in H. C. Pilot (1978) in "Fundamentals of Oncology," Marcel Dekker (Ed.), New York pp 15-28. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell." A dysplastic cell resembles an immature epithelial cell, is generally spatially disorganized within the tissue and loses its specialized structures and functions. During the intermediate stages of neoplastic progression, an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive i.e., they either invade adjacent tissues, or are shed from the primary site and circulate through the blood and lymph to other locations in the body where they initiate secondary cancers. As used herein, the term "cancer cell" encompasses both pre-malignant and malignant cancer cells.

Interest in histone deacetylase enzymes (HDACs) as targets for pharmaceutical development has centered on the role of HDACs in regulating genes associated with cell-cycle progression and the development and progression of cancer. Several studies have shown that treatment of various cell lines with HDAC inhibitors leads to hyper acetylation of histone proteins and cell-cycle arrest in late G1 phase or at the G2/M transition. Genes involved in the cell cycle that have been shown to be up regulated by HDAC inhibitors include p21, p27, p53 and cyclin E. Cyclin A and cyclin D have been reported to be down regulated by HDAC inhibitors. In tumor cell lines, several studies have shown that treatment with HDAC inhibitors lead to growth inhibition, growth arrest, terminal differentiation and/or apoptosis. In vivo studies have demonstrated growth inhibition of tumors and a reduction in tumor metastasis as a result of treatment with HDAC inhibitors.

The compound described herein can be administered to a subject as part of a therapeutic application. In general, the method can be characterized as including a step of administering a therapeutically effective amount of the compound to subject in need thereof.

Thus, the compounds described herein can be used for treating a disease state when HDAC activity contributes to the pathology or symptomology of the disease. Generally, the method comprising administering a therapeutically effective amount of a compound disclosed herein to a subject in need of treatment.

In one embodiment, the compounds and method can used in treating a subject afflicted with cancer, a precancerous condition and/or metastasis. As used herein, an anti-cancer treatment aims to reduce, prevent or eliminate cancer cells or the spread of cancer cells or the symptoms of cancer in the local, regional or systemic circulation. Anti-cancer treatment also means the direct treatment of tumors, for example by reducing or stabilizing their number or their size (curative effect), but also by preventing the in situ progression of tumor cells or their diffusion, or the establishment of tumors; this also includes the treatment of deleterious effects linked to the presence of such tumors, in particular the attenuation of symptoms observed in a patient or an improvement in quality of life. By "reduced" in the context of cancer is meant reduction of at least 10% in the growth rate of a tumor or the size of a tumor or cancer cell burden.

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. A metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including Glioblastomas and medulloblastomas; cervical cancer; choriocarcinoma; colon cancer, endometrial cancer, esophageal cancer, gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer, rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer, testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, Glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan.

As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers. Examples of cancers that can be treated with the compounds of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma. The compounds of the invention are useful for treating patients who have been previously treated for cancer, as well as those who have not previously been treated for cancer. Indeed, the methods and compositions of this invention can be used in first-line and second-line cancer treatments.

In some embodiments, the cancer or metastasis is selected from the group consisting of platinum susceptible or resistant tumors including breast, head and neck, ovarian, testicular, pancreatic, oral-esophageal, gastrointestinal, liver, gall bladder, lung, melanoma, skin cancer, sarcomas, blood cancers, brain tumors including glioblastomas, and tumors of neuroectodermal origin.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

In some embodiments, the cancer is T-cell lymphoma, leukemia, or neuroblastoma.

Pharmaceutical Compositions

For administration to a subject, the compounds described herein can be provided in pharmaceutically acceptable (e.g., sterile) compositions. Accordingly, another aspect described herein is a pharmaceutical composition comprising a compound according to formula (I) and a pharmaceutically acceptable carrier. These pharmaceutically acceptable compositions comprise an effective amount of one or more of the compounds described herein, formulated together with one or more pharmaceutically acceptable carriers (additives) and/or diluents. As described in detail below, the pharmaceutical compositions of the present disclosure can be specifically formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 35 3,270,960, content of all of which is herein incorporated by reference.

Formulations can optionally further comprise one or more cylcodextrins. In various cases, cyclodextrins are α-cyclodextrins, β-cyclodextrins, γ-cyclodextrins, and/or δ-cyclodextrins. In some embodiments, the cyclodextrins are modified cyclodextrins. Specific modifications include, but are not limited to, hydroxyalkyl ethers and sulfoalkyl ethers. In some embodiments, the modified cyclodextrins are sulfobutylether-1-β-cyclodextrin, sulfobutylether-4-β-cyclodextrin, sulfobutylether-7-β-cyclodextrin, and/or hydroxypropylether β-cyclodextrin. In one embodiment, the modified cyclodextrin comprises sulfobutylether-7-β-cyclodextrin.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar, (14) buffering agents, such as magnesium hydroxide and aluminum hydroxide; (15) alginic acid; (16) pyrogen-free water, (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

For liquid formulations, pharmaceutically acceptable carriers can be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions, or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include one or more of the following components: a sterile diluent, including water for injection, saline solution, fixed oils, polyethylene glycols, glycerine, propylene glycol and other synthetic solvents; antibacterial agents, including benzyl alcohol and methyl parabens; anti-oxidants, including ascorbic acid or sodium bisulfite; chelating agents, including ethylenediaminetetraacetic acid (EDTA); buffers, including acetates, citrates and phosphates, and agents for the adjustment of tonicity, including sodium chloride and dextrose. The pH can be adjusted with acids or bases, including hydrochloric acid and sodium hydroxide.

Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As indicated above, the compositions can further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

It is especially advantageous to formulate oral and intravenous compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration.

The amount of a compound described herein that can be combined with a carrier material to produce a single dosage form will generally be an effective amount of the compound. A pharmaceutical composition typically contains an amount of at least 0.01 weight % of active ingredient, i.e., a compound of this disclosure, per weight of total pharmaceutical composition. Generally out of one hundred percent, this amount will range from about 0.01% to 99% of the compound, preferably from about 5% to about 70%, most preferably from 10% to about 30%. A weight % is a ratio by weight of active ingredient to total composition. Thus, for example, 0.1 weight % is 0.1 grams of the compound per 100 grams of total composition.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic, or oily solutions and the like as detailed above.

For intravenous administration, glucuronic acid, L-lactic acid, acetic acid, citric acid or any pharmaceutically acceptable acid/conjugate base with reasonable buffering capacity in the pH range acceptable for intravenous administration can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12.

Subcutaneous formulations can be prepared according to procedures well known in the art at a pH in the range between about 5 and about 12, which include suitable buffers and isotonicity agents. They can be formulated to deliver a daily dose of the active agent in one or more daily subcutaneous administrations. The choice of appropriate buffer and pH of a formulation, depending on solubility of one or more compounds to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12.

Formulations for Oral Administration

Formulations of the invention suitable for oral administration can be in the form of a solid, gel or liquid. For example, the formulation can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like. More specific examples of oral tablets include compressed, chewable lozenges and tablets that can be enteric-coated, sugarcoated or film-coated. Examples of capsules include hard or soft gelatin capsules. Granules and powders can be provided in non-effervescent or effervescent forms. Each can be combined with other ingredients known to those skilled in the art.

In certain embodiments, the compound described herein can be provided as solid dosage forms, preferably capsules or tablets. The tablets, pills, capsules, troches and the like can optionally contain one or more of the following ingredients, or compounds of a similar nature: a binder, a diluent; a disintegrating agent; a lubricant; a glidant; a sweetening agent; and a flavoring agent.

Examples of binders that can be used include, but are not limited to, microcrystalline cellulose, gum tragacanth, glucose solution, acacia mucilage, gelatin solution, sucrose and starch paste.

Examples of lubricants that can be used include, but are not limited to, talc, starch, magnesium or calcium stearate, lycopodium and stearic acid.

Examples of diluents that can be used include, but are not limited to, lactose, sucrose, starch, kaolin, salt, mannitol and dicalcium phosphate.

Examples of glidants that can be used include, but are not limited to, colloidal silicon dioxide.

Examples of disintegrating agents that can be used include, but are not limited to, crosscarmellose sodium, sodium starch glycolate, alginic acid, corn starch, potato starch, bentonite, methylcellulose, agar and carboxymethylcellulose.

Examples of coloring agents that can be used include, but are not limited to, any of the approved certified water soluble FD and C dyes, mixtures thereof; and water insoluble FD and C dyes suspended on alumina hydrate.

Examples of sweetening agents that can be used include, but are not limited to, sucrose, lactose, mannitol and artificial sweetening agents such as sodium cyclamate and saccharin, and any number of spray-dried flavors.

Examples of flavoring agents that can be used include, but are not limited to, natural flavors extracted from plants such as fruits and synthetic blends of compounds that produce a pleasant sensation, such as, but not limited to peppermint and methyl salicylate.

Examples of wetting agents that can be used include, but are not limited to, propylene glycol monostearate, sorbitan monooleate, diethylene glycol monolaurate and polyoxyethylene lauryl ether.

Examples of anti-emetic coatings that can be used include, but are not limited to, fatty acids, fats, waxes, shellac, ammoniated shellac and cellulose acetate phthalates.

Examples of film coatings that can be used include, but are not limited to, hydroxyethylcellulose, sodium carboxymethylcellulose, polyethylene glycol 4000 (PEG 4000) and cellulose acetate phthalate.

If oral administration is desired, the salt of the compound can optionally be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can optionally additionally comprise a liquid carrier such as a fatty oil. In addition, dosage unit forms can optionally additionally comprise various other materials that modify the physical form of the dosage unit, for example, coatings of sugar and other enteric agents.

Compounds according to the present invention can also be administered as a component of an elixir, suspension, syrup, wafer, sprinkle, chewing gum or the like. A syrup can optionally comprise, in addition to the active compounds, sucrose as a sweetening agent and certain preservatives, dyes and colorings and flavors.

The compounds described herein can also be mixed with other active materials that do not impair the desired action, or with materials that supplement the desired action. For example, if a compound is used for treating cancer, it can be used with other anti-cancer agents.

Examples of pharmaceutically acceptable carriers that can be included in tablets comprising the compounds described herien include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines.

Sugar-coated tablets can be compressed tablets to which different layers of pharmaceutically acceptable substances are applied. Film-coated tablets can be compressed tablets that have been coated with polymers or other suitable coating. Multiple compressed tablets can be compressed tablets made by more than one compression cycle utilizing the pharmaceutically acceptable substances previously mentioned. Coloring agents can also be used in tablets. Flavoring and sweetening agents can be used in tablets, and are especially useful in the formation of chewable tablets and lozenges.

Examples of liquid oral dosage forms that can be used include, but are not limited to, aqueous solutions, emulsions, suspensions, solutions and/or suspensions reconstituted from non-effervescent granules and effervescent preparations reconstituted from effervescent granules.

Examples of aqueous solutions that can be used include, but are not limited to, elixirs and syrups. As used herein, elixirs refer to clear, sweetened, hydroalcoholic preparations. Examples of pharmaceutically acceptable carriers that can be used in elixirs include, but are not limited to solvents. Particular examples of solvents that can be used include glycerin, sorbitol, ethyl alcohol and syrup. As used herein, syrups refer to concentrated aqueous solutions of a sugar, for example, sucrose. Syrups can optionally further comprise a preservative.

Emulsions refer to two-phase systems in which one liquid is dispersed in the form of small globules throughout another liquid. Emulsions can optionally be oil-in-water or water-in oil emulsions. Examples of pharmaceutically acceptable carriers that can be used in emulsions include, but are not limited to non-aqueous liquids, emulsifying agents and preservatives.

Examples of pharmaceutically acceptable substances that can be used in non-effervescent granules, to be reconstituted into a liquid oral dosage form, include diluents, sweeteners and wetting agents.

Examples of pharmaceutically acceptable substances that can be used in effervescent granules, to be reconstituted into a liquid oral dosage form, include organic acids and a source of carbon dioxide.

Coloring and flavoring agents can optionally be used in all of the above dosage forms.

Particular examples of preservatives that can be used include glycerin, methyl and propylparaben, benzoic add, sodium benzoate and alcohol.

Particular examples of non-aqueous liquids that can be used in emulsions include mineral oil and cottonseed oil.

Particular examples of emulsifying agents that can be used include gelatin, acacia, tragacanth, bentonite, and surfactants such as polyoxyethylene sorbitan monooleate.

Particular examples of suspending agents that can be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that can be used include propylene glycol monostearate, sorbitan monooleate, diethylene glycol monolaurate and polyoxyethylene lauryl ether.

Particular examples of organic acids that can be used include citric and tartaric acid.

Sources of carbon dioxide that can be used in effervescent compositions include sodium bicarbonate and sodium carbonate. Coloring agents include any of the approved certified water-soluble FD and C dyes, and mixtures thereof.

Particular examples of flavoring agents that can be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545, content of all of which is incorporated herein by reference in their entirety. For a liquid dosage form, the solution, e.g., for example, in a polyethylene glycol, can be diluted with a sufficient quantity of a pharmaceutically acceptable liquid carrier, e.g. water, to be easily measured for administration.

Alternatively, liquid or semi-solid oral formulations can be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603, content of both of which is incorporated herein by reference in their entirety.

Injectables, Solutions, and Emulsions

The present invention is also directed to compositions designed to administer the compounds described herein by parenteral administration, generally characterized by injection, either subcutaneously, intramuscularly or intravenously. Injectables can be prepared in any conventional form, for example as liquid solutions or suspensions, solid forms suitable for solution or suspension in liquid prior to injection, or as emulsions.

Examples of excipients that can be used in conjunction with injectables according to the present invention include, but are not limited to water, saline, dextrose, glycerol or ethanol. The injectable compositions can also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained-release system, such that a constant level of dosage is maintained is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that can optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that can optionally be used include Sodium Chloride Injection, Ringers Injection, Isotonic Dextrose Injection, Sterile Water Injection, Dextrose and Lactated Ringers Injection.

Examples of nonaqueous parenteral vehicles that can optionally be used include fixed oils of vegetable origin, cottonseed oil, corn oil, sesame oil and peanut oil.

Antimicrobial agents in bacteriostatic or fungistatic concentrations can be added to parenteral preparations, particularly when the preparations are packaged in multiple-dose containers and thus designed to be stored and multiple aliquots to be removed. Examples of antimicrobial agents that can be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that can be used include sodium chloride and dextrose. Examples of buffers that can be used include phosphate and citrate. Examples of antioxidants that can be used include sodium bisulfate. Examples of local anesthetics that can be used include procaine hydrochloride. Examples of suspending and dispersing agents that can be used include sodium carboxymethylcellulose, hydroxypropyl methylcellulose and polyvinylpyrrolidone. Examples of emulsifying agents that can be used include Polysorbate 80 (TWEEN 80). A sequestering or chelating agent of metal ions includes EDTA.

Pharmaceutical carriers can also optionally include ethyl alcohol, polyethylene glycol and propylene glycol for water miscible vehicles and sodium hydroxide, hydrochloric acid, citric acid or lactic acid for pH adjustment.

The concentration of the compound in the parenteral formulation can be adjusted so that an injection administers a pharmaceutically effective amount sufficient to produce the desired pharmacological effect.

Injectables can be designed for local and systemic administration.

Unit-dose parenteral preparations can be packaged in an ampoule, a vial or a syringe with a needle. All preparations for parenteral administration should be sterile, as is known and practiced in the art.

The compounds described herein can optionally be suspended in micronized or other suitable form or can be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and can be empirically determined.

Lyophilized Powders

The compounds described herein can also be prepared as lyophilized powders, which can be reconstituted for administration as solutions, emulsions and other mixtures. The lyophilized powders can also be formulated as solids or gels.

Sterile, lyophilized powder can be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder can optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a compound described herein is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial can contain a single dosage or multiple dosages of the compound described herein.

Topical Administration

The compounds described herein can also be administered as topical mixtures. Topical mixtures can be used for local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds described herein can be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a micro fine powder for insufflation, alone or in combination with an inert carrier such as lactose. In such a case, the particles of the formulation will typically have diameters of less than 50 microns, preferably less than 10 microns.

The compounds described herein can also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the compound alone or in combination with other pharmaceutically acceptable excipients can also be administered.

Formulations for Other Routes of Administrations

Depending upon the disease state being treated, other routes of administration, such as topical application, transdermal patches, and rectal administration, can also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

Examples of Formulations

The following are particular examples of oral, intravenous and tablet formulations that can optionally be used with compounds of the present invention. It is noted that these formulations can be varied depending on the particular compound being used and the indication for which the formulation is going to be used.

Oral formulation: (i) compound described herein, 10-100 mg; (ii) citric acid monohydrate, 105 mg; (iii) sodium hydroxide, 18 mg; (iv) flavoring; and (v) water, q.s. to 100 ml.

Intravenous formulation: (i) compound described herein, 0.1-10 mg; (ii) dextrose monohydrate, q.s. to make isotonic; (iii) citric acid monohydrate, 1.05 mg; (iv) sodium hydroxide, 0.18 mg; and (v) water for injection, q.s. to 1.0 ml.

Tablet formulation: (i) compound described herein, 1%; (ii) microcrystalline cellulose, 73%; (iii) stearic acid, 25%; and (iv) colloidal silica, 1%.

Kits

The invention is also directed to kits and other articles of manufacture for treating diseases associated with HDACs. It is noted that diseases are intended to cover all conditions for when HDAC activity contributes to the pathology and/or symptomology of the condition.

In one embodiment, a kit is provided that comprises a composition comprising at least one compound disclosed herein in combination with instructions. The instructions can indicate the disease state for which the composition is to be administered, storage information, dosing information and/or instructions regarding how to administer the composition. The kit can also comprise packaging materials. The packaging material can comprise a container for housing the composition. The kit can also optionally comprise additional components, such as syringes for administration of the composition. The kit can comprise the composition in single or multiple dose forms.

In another embodiment, an article of manufacture is provided that comprises a composition comprising at least one compound disclosed herein in combination with packaging materials. The packaging material can comprise a container for housing the composition. The container can optionally comprise a label indicating the disease state for which the composition is to be administered, storage information, dosing information and/or instructions regarding how to administer the composition. The kit can also optionally comprise additional components, such as syringes for administration of the composition. The kit can comprise the composition in single or multiple dose forms.

It is noted that the packaging material used in kits and articles of manufacture according to the present invention can form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets can be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or can have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Combination Therapy

The treatment methods described herein can be used with one or more additional therapies, e.g., anti-cancer therapies. Exemplary anti-cancer therapies include, but are not limited to, surgery, chemotherapy, radiation therapy, and the like.

The compounds described herein can be used or administrated to a subject in combination with another pharmaceutically active agent or treatment modality for a particular indication. Exemplary pharmaceutically active compound include, but are not limited to, those found in *Harrison's Principles of Internal Medicine*, 13$^{th}$ Edition, Eds. T. R. Harrison et al. McGraw-Hill N.Y., N.Y.; Physicians' Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Wide variety therapeutic agents can have a therapeutic additive or synergistic effect with the compounds described herein. Such therapeutic agents can additively or synergistically combine with the compounds described herein to inhibit undesirable cell growth, such as inappropriate cell growth resulting in undesirable benign conditions or tumor growth.

The term "synergistic" as used herein is defined to mean a combination of components wherein the activity of the combination is greater than the additive of the individual activities of each component of the combination. In some embodiments, the activity of the combination is at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, at least 10-fold, at least 50-fold, at least 100-fold or greater than the additive of the individual activities of each component of the combination.

Examples of therapeutic agents that can be used in combination with compounds described herein include, but are not limited to, anticancer agents, alkylating agents, antibiotic agents, antimetabolic agents, hormonal agents, plant-derived agents, and biologic agents.

In some embodiments, the therapeutic agent, e.g., the drug is an anti-cancer agent. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., paclitaxel), and angiogenesis inhibitors. Exemplary anti-cancer compounds include, but are not limited to, paclitaxel (TAXOL®); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a compound described herein and an alkylating agent can have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interferes with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a HDAC inhibitor and an antibiotic agent can have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a HDAC inhibitor and a antimetabolic agent can have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents can serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including a HDAC inhibitor and a hormonal agent can have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a HDAC inhibitor and a plant-derived agent can have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a HDAC inhibitor and a biologic agent can have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that can be used in conjunction with HDAC inhibitor include, but are not limited to, interleukin 2 (IL-2), and interleukin 4 (IL-4), interleukin 12 (IL-12). Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that can be used in conjunction with a HDAC inhibitor include those cytokines that exert profound effects on hematopoiesis and immune functions. Examples of such cytokines include, but are not limited to erythropoietin, granulocyte-CSF (filgrastin), and granulocyte, macrophage CSF (sargramostim). These cytokines can be used in conjunction with a HDAC inhibitor to reduce chemotherapy induced myelopoietic toxicity. Other immuno-modulating agents other than cytokines can also be used in conjunction with a HDAC inhibitor to inhibit abnormal cell growth. Examples of such immunomodulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein.

Combination Therapy Including

The compounds described herein and HERCEPTIN® can have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant $CD20^+$ pre-B and mature B cells. RITUXAN® is used as single agent for the treatment of patients with relapsed or refractory low-grade or follicular, $CD20^+$, B cell nonHodgkin's lymphoma. Combination therapy including the compounds disclosed herein and RITUXAN® can have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a HDAC inhibitor and a tumor suppressor can have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancers), melanoma associated antigens (MART-1, gplOO, MAGE 1,3 tyrosinase), papillomavirus E6 and E7 fragments, whole cells or portions/lysates of antologous tumor cells and allogeneic tumor cells.

An adjuvant can be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and Cytoxan, a chemotherapeutic agent which is believe to reduce tumor-induced suppression when given in low doses.

In certain embodiments, the method also includes use or co-administration to the subject an effective amount of an anti-cancer agent. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

In some embodiments, a compound described herein is the only pharmaceutically active agent in the composition administered to the subject.

Embodiments of the various aspects disclosed herein can be described by one or more of the number paragraphs:

1. A compound of formula (I):

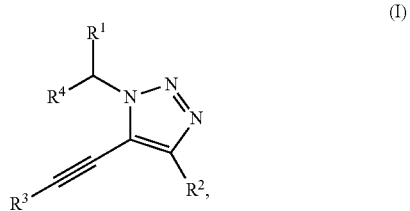

wherein:

$R^1$ is optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, halogen, CN, $CF_3$, $C(O)R^5$, $CO_2R^5$, $C(O)N(R^6)_2$, $OR^5$, $SR^5$, $SOR^5$, $SO_2R^5$, $SSR^5N(R^6)_2$, $NHR^6$, $NR^6C(O)R^5$, or $NO_2$, each of which can be optionally substituted, wherein the backbone of alkyl, alkenyl, or alkynyl optionally comprises one or more heteroatoms, and wherein the carbon to which $R^1$ is attached has the S stereochemistry;

$R^2$ is optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, halogen, CN, $CF_3$, $C(O)R^5$, $CO_2R^5$, $C(O)N(R^6)_2$, $OR^5$, $SR^5$, $SOR^5$, $SO_2R^5$, $OSO_2R^5$, $SSR^5$, $N(R^6)_2$, $NHR^6$, $NR^6C(O)R^5$, or $NO_2$, each of which can be optionally substituted, and wherein the backbone of alkyl, alkenyl, or alkynyl optionally comprises one or more heteroatoms;

$R^3$ is H, optionally substituted linear or branched alkyl, optionally substituted linear or branched alkenyl, optionally substituted linear or branched alkynyl, optionally substituted cyclyl, optionally substituted heterocyclcyl, or optionally substituted aryl, optionally substituted heteroaryl;

$R^4$ is a substituent capable of complexing with a histone deacetylase (HDAC) catalytic site or a metal ion, provided that $R^4$ is not an ester, $CO_2H$, or methyl hydroxamide;

$R^5$ is independently for each occurrence H, optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, wherein the backbone of alkyl, alkenyl, or alkynyl optionally comprises one or more heteroatoms;

$R^6$ is independently for each occurrence H, optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, $C(O)R^5$, $CO_2R^5$, or $SO_2R^5$, each of which can be optionally substituted, wherein the backbone of alkyl, alkenyl, or alkynyl optionally comprises one or more heteroatoms; and a hydrate, salt, solvate, or ester thereof.

2. The compound of paragraph 1, wherein R¹ is selected from the group consisting of linear or branched $C_1$-$C_{10}$ alkyl, aryl, —$CH_2$-aryl, and —$CH_2$-heteroaryl, each of which can be optionally substituted.

3. The compound of paragraph 1 or 2, wherein R¹ is selected from the group consisting of benzyl, 2-propyl, 1H-indol-3-yl-methyl, phenyl, and indol-3-yl-methyl.

4. The compound of any of paragraphs 1-3, wherein R² is linear or branched $C_1$-$C_{10}$ alkyl, cyclyl, heterocyclyl, aryl, or heteroaryl, each of which can be optionally substituted.

5. The compound of any of paragraphs 1-4, wherein R² is phenyl.

6. The compound of any of paragraphs 1-5, wherein R³ is $C_1$-$C_{10}$alkyl; aryl; heteroaryl; cyclyl; heterocyclyl; $C_1$-$C_6$alkyl substituted with aryl, heteroaryl, cyclyl, heterocyclyl, OR⁵, SR⁵, or —$OSO_2R^5$, wherein R⁵ is H, alkyl, alkenyl, alkynyl, aryl, heteroaryl, cyclyl, heterocyclyl, and each of which can be optionally substituted.

7. The compound of any of paragraphs 1-6, wherein R³ is 2-phenyl ethyl; phenylthio methyl; 4-fluoro phenyl; phenoxy methyl; 4-methoxy phenyl; 4-bromo phenyl; 4-t-butyl phenyl; phenyl; 4-cyano phenyl; 2-pyridinyl; 3-pyridinyl; 2-pyranyloxy ethyl; cyclopropyl; isoindoline-1,3-dionyl methyl; 4-phenyl phenyl; 4-ethyl phenyl; cyclopentyl methyl; 3-methoxy phenyl; 4-(N,N-dimethylamino) phenyl; 3-chloro phenyl; 3,5-dimethoxy phenyl; 2,4,5-trimethyl phenyl; 2-methoxy phenyl; 2-methyl-4-methoxyphenyl; 4-acerylamino phenyl; 4-chloro phenyl; 4-methyl-phenylsulfonyloxy methyl; and phenylsulfonyloxy methyl.

8. The compound of paragraph 8, wherein R³ is phenyl or cyclopropyl.

9. The compound of any of paragraphs 1-8, wherein R⁴ is —C(O)R⁷, —NH—P(O)OR⁵—R⁵, —$SO_2R^5$, —$SO_2N(R^6)_2$, —$SO_2NR^6OR^5$, or —SR⁵, wherein R⁷ is independently for each occurrence optionally substituted alkyl, NR⁶OR⁵, amino, —C(O)N(R⁶)₂, optionally substituted cyclyl, optionally substituted heterocyclyl, optionally substituted aryl; optionally substituted heteroaryl; optionally substituted alkylamino, optionally substituted arylamino, or optionally substituted heteroarylamino.

10. The compound of paragraph 9, wherein R⁷ is NHOR⁵; —$SO_2NHOR^5$; optionally substituted phenylamino; optionally substituted aza-aryl amino; optionally substituted aza-cyclyl; optionally substituted 3-8 membered heterocyclyl; or optionally substituted $C_1$-$C_6$ alkyl.

11. The compound of any of paragraphs 1-10, wherein R⁴ is —C(O)NHOH, —$CF_3$, —$SO_2NHOH$, —C(O)$CH_2$OH, —C(O)$CH_2$SH, acetyl (—C(O)$CH_3$), —C(O)$CH_2CH_3$, 2-amino-phenylamino-carbonyl; 2-hydroxy-phenylamino-carbonyl; thiazolyl-amino carbonyl; oxazolylamino carbonyl; 4,5-dihydro-oxazolylamino carbonyl; or oxiranyl carbonyl.

12. The compound of paragraph 11, wherein R⁴ is hydroxamic acid (—C(O)NHOH).

13. The compound of paragraph 1, wherein the compound is a compound of formula (IB):

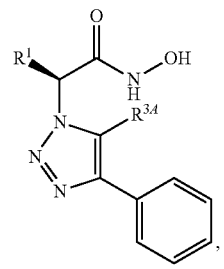

(IB)

wherein:
R¹ is benzyl, 2-propyl, 1H-indol-3-yl-methyl, or phenyl; and
R^{3A} is selected from

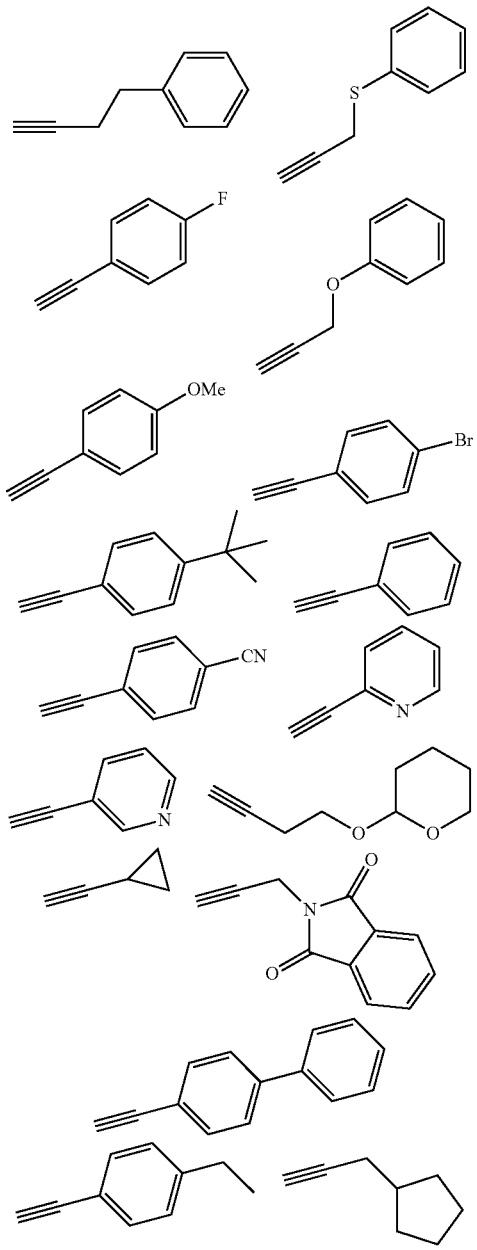

-continued

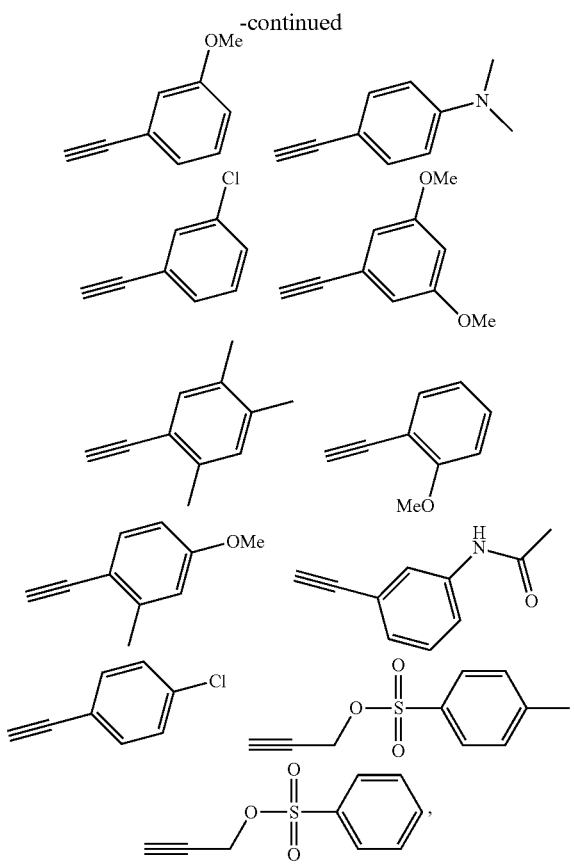

wherein $R^{3,4}$ is connected via the carbon on the terminal end of the alkyne shown in the structures.

14. The compound of paragraph 13, wherein the compound is

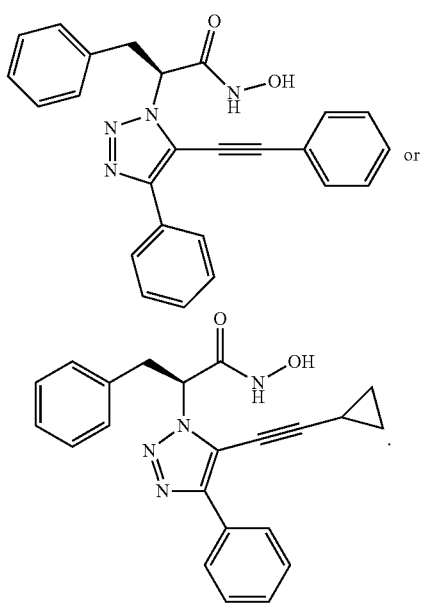

15. A pharmaceutical composition comprising a compound of any of paragraphs 1-14 and a pharmaceutically acceptable diluent, excipient, or carrier.

16. The pharmaceutical composition of paragraph 15, wherein the pharmaceutical composition is formulated for intravenous injection, subcutaneous injection, oral administration, inhalation, nasal administration, topical administration, ophthalmic administration or optic administration.

17. The pharmaceutical composition of paragraph 15 or 16, wherein the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop 18. A method of treating a disease state when a histone deacetylase activity contributes to the pathology or symptomology of the disease, the method comprising administering a therapeutically effective amount of a compound of any of paragraphs 1-14 to a subject in need thereof.

19. A method of treating cancer, the method comprising administering a therapeutically effective amount of a compound of any of paragraphs 1-14 to a subject in need thereof.

20. The method of paragraph 19, wherein the cancer is selected from the group consisting of adenocarcinoma; adult T-cell leukemia/lymphoma; AIDS-associated leukemia; basal cell carcinoma; biliary tract cancer, bladder cancer; blastoma; brain cancer including Glioblastomas and medulloblastomas; breast cancer; cervical cancer, choriocarcinoma; chronic myelogenous leukemia; colon cancer; colorectal cancer, endometrial carcinoma; esophageal cancer, esticular cancer, gastric cancer; gastrointestinal cancer; Glioblastoma; hairy cell leukemia; hematological neoplasms including acute lymphocytic and myelogenous leukemia; Hodgkin's and non-Hodgkin's lymphoma; intraepithelial neoplasms including Bowen's disease and Paget's disease; Leukemia; liver cancer such as hepatic carcinoma and hepatoma; lung cancer; lymphomas including Hodgkin's disease and lymphocytic lymphomas; melanoma; multiple myeloma; neuroblastomas; non-small cell lung cancer; oral cancer including squamous cell carcinoma; ovarian cancer including those arising from epithelial cells, stromal cells, germ cells and mesenchymal cells; pancreatic cancer; prostate cancer, rectal cancer; renal cancer including adenocarcinoma, kidney cancer, and Wilms' tumor; salivary gland carcinoma; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; small-cell lung cancer; squamous cell cancer, T-cell acute lymphoblastic leukemia/lymphoma; T-cell lymphoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; vulval cancer, and any combinations thereof.

21. The method of paragraph 19 or 20, wherein the cancer is T-cell lymphoma, leukemia, or neuroblastoma.

22. The method of any of paragraphs 18-21, wherein the said administering is by injection, infusion, instillation, inhalation, or ingestion.

23. The method of paragraph 22, wherein said injection is intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, or intrasternal injection.

24. The method of any of paragraphs 18-23, wherein the therapeutically effective amount of the compound is 1 µg/kg to 150 mg/kg of bodyweight.
25. The method of any of paragraphs 18-24, wherein said administering is daily administration.
26. The method of any of paragraphs 18-25, further comprising administering one or more additional anti-cancer therapy to the subject.
27. The method of paragraph 26, wherein the additional therapies are selected from the group consisting of surgery, chemotherapy, radiation therapy, thermotherapy, immunotherapy, hormone therapy, laser therapy, anti-angiogenic therapy, and any combinations thereof.
28. The method of paragraph any of paragraphs 18-27, further comprising administering to the subject a second therapeutic agent, selected from the group consisting of abarelix; actinomycin D; Aldesleukin; Alemtuzumab; alitretinoin; allopurinol; altretamine; amifostine; anastrozole; arsenic trioxide; Asparaginase; Azacitidine; BCG Live; bevacizumab; bexarotene; bexarotene capsules; bexarotene gel; bleomycin; bortezomib; busulfan; busulfan intravenous; busulfanoral; calusterone; capecitabine; carboplatin; carmustine; carmustine with Polifeprosan Implant; celecoxib; cetuximab; chlorambucil; cisplatin; cladribine; clofarabine; cyclophosphamide; cytarabine; cytarabine liposomal; dacarbazine; dactinomycin; Darbepoetin alfa; dasatinib; daunomycin; daunorubicin; daunorubicin liposomal; decitabine; denileukin; Denileukin diftitox; dexrazoxane; docetaxel; doxorubicin; doxorubicin liposomal; Dromostanolone propionate; Elliott's B Solution; Epirubicin; Epoetin alfa; Epoetin alfa estramustine; erlotinib; estramustine; etoposide (VP-16); etoposide phosphate; exemestane; Filgrastim; floxuridine; floxuridine (intraarterial); fludarabine; fluorouracil (5-FU); fulvestrant; gefitinib; gemcitabine; gemtuzumab ozogamicin; germicitibine; goserelin acetate; histrelin acetate; hydroxyurea; Ibritumomab Tiuxetan; idarubicin; ifosfamide; imatinib mesylate; interferon alfa 2a; Interferon alfa-2b; irinotecan; lenalidomide; letrozole; leucovorin; Leuprolide Acetate; levamisole; LOddC; lomustine (CCNU); mechlorethamine (nitrogenmustard); megestrol acetate; melphalan (L-PAM); mercaptopurine (6-MP); mesna; methotrexate; methoxsalen; mithramycin; mithramycin; mitomycin C; mitotane; mitoxantrone; nandrolone phenpropionate; nelarabine; Nofetumomab; Oprelvekin; oxaliplatin; paclitaxel (taxol); paclitaxel protein-bound particles; paclitaxel-carbohydrate conjugates; palifermin; pamidronate; panitumumab; pegademase; Pegaspargase; Pegfilgrastim; pemetrexed disodium; pentostatin; pipobroman; plicamycin; porfimer sodium; procarbazine; quinacrine; Rasburicase; Rituximab; Sargramostim; streptozocin; sunitinib maleate; talbuvidine (LDT); talc; tamoxifen; temozolomide; teniposide (VM-26); testolactone; thalidomide; thioguanine (6-TG); thiotepa; topotecan; toremifene; Tositumomab or I$^{131}$-Tositumomab; Trastuzumab; tretinoin (ATRA); Uracil Mustard; valrubicin; valtorcitabine (monoval LDC); vinblastine; vincristine; vinorelbine; vorinostat; zoledronate; zoledronic acid; and any combinations thereof.
29. The method of any of paragraphs 18-28, wherein the subject is a mammal.
30. The method of any of paragraphs 18-29, wherein the subject is a human.
31. Use of a compound of any of paragraphs 1-14 for the preparation of a medicament for the treatment of a disease state when a histone deacetylase activity contributes to the pathology or symptomology of the disease.
32. Use of a compound of any of paragraphs 1-14 for the preparation of a medicament for the treatment of cancer.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

As used herein, the term, "aromatic" means a moiety wherein the constituent atoms make up an unsaturated ring system, all atoms in the ring system are $sp^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, 1-propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals.

Prefixes $C_x$ and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =$CR_aR_b$. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, benzyl, phenyl, naphthyl, anthracenyl, azulenyl, fluorenyl, indanyl, indenyl, naphthyl, phenyl, tetrahydronaphthyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^C$, —N$^+$(O$^-$)=, —O—, —S— or —S(O)$_2$—, —OS(O)$_2$—, and —SS—, wherein R$^c$ is H or a further substituent.

The term "hydroxy" means the radical —OH.

The term "thiol" means the radical —SH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkynyl, amide, amino, aminoalkyl, aralkyl, aralkylsulfonamido, arenesulfonamido, arenesulfonyl, aromatic, aryl, arylamino, arylcarbanoyl, aryloxy, carbamoyl, carbonyl, carboxy, cyano, cycloalkyl, cycloalkylene, ester, haloalkyl, halogen, heteroaryl, heterocyclyl, hydroxy, hydroxyalkyl, iminoketone, ketone, mercapto, nitro, oxaalkyl, oxo, oxoalkyl, and ureido, moieties, each of which may optionally also be substituted or unsubstituted. In some cases, two substituents, together with the carbon(s) to which they are attached to, can form a ring.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids, sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH3) as well as —$CR_aR_bR_c$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

In some embodiments, the compounds described herein can be in the form of a prodrug. The term "prodrug" as used herein refers to compounds that can be converted via some chemical or physiological process (e.g., enzymatic processes and metabolic hydrolysis) to compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [Symp.] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273

(1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which are herein incorporated by reference in its entirety.

The term "protected derivatives" means derivatives of compounds described herein in which a reactive site or sites are blocked with protecting groups. Protected derivatives are useful in the preparation of compounds or in themselves can be active. A comprehensive list of suitable protecting groups can be found in T. W. Greene, *Protecting Groups in Organic Synthesis,* 3rd edition, John Wiley & Sons, Inc. 1999.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center, although all enantiomers are stereoisomers, not all stereoisomers are enantiomers) or "optical isomers" (because of the optical activity of pure enantiomers, which is the ability of different pure enantiomers to rotate plane polarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+)" and "(−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F(+) and F(−) (where the sum of F(+) and F(−)=1). The enantiomeric excess is defined as *F(+)−F(−)* and the percent enantiomeric excess by 100× *F(+)−F(−)*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer, typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereo-preferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The term "RT" refers to room temperature, about 20° C. to 25° C.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects. The compounds described herein are effective in treating various types of cancer.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount, for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to treat domesticated animals and/or pets.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The phrase "therapeutically-effective amount" as used herein means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to effect such treatment for the disease.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a compound as disclosed herein can be about 0.01 µM to about 10 µM, about 0.2 µM to about 5 µM, or about 0.8 to about 3 µM in a subject, such as a rat, dog, or human.

Generally, the compositions are administered so that a compound of the disclosure herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The compound can be administered as a single bolus or multiple boluses, as a continuous infusion, or a combination thereof. For example, the compound can be administered as a single bolus initially, and then administered as a continuous infusion following the bolus. The rate of the infusion can be any rate sufficient to maintain effective plasma concentration. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The terms "co-administration" or the like, as used herein, are meant to encompass administration of the selected therapeutic agents to a single patient, and are intended to include treatment regimens in which the agents are administered by the same or different route of administration or at the same or different time.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to sustained progression, expediting remission, inducing remission, augmenting remission, speeding recovery, increasing efficacy of or decreasing resistance to alternative therapeutics, or a combination thereof. "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment symptoms are secondary. "Primary" refers to a symptom that is a direct result of a disorder, e.g., diabetes, while, secondary refers to a symptom that is derived from or consequent to a primary cause. Symptoms may be any manifestation of a disease or pathological condition.

Accordingly, as used herein, the term "treatment" or "treating" includes any administration of a compound described herein and includes: (i) preventing the disease from occurring in a subject which may be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Efficacy of treatment is determined in association with any known method for diagnosing the disorder. Alleviation of one or more symptoms of the disorder indicates that the compound confers a clinical benefit. Any of the therapeutic methods described to above can be applied to any suitable subject including, for example, mammals such as dogs, cats, cows, horses, rabbits, monkeys, and most preferably, humans.

The disclosure is further illustrated by the following examples which should not be construed as limiting. The examples are illustrative only, and are not intended to limit, in any manner, any of the aspects described herein. The following examples do not in any way limit the invention.

EXAMPLES

Histone deacetylase (HDAC) enzymes are an important family of proteins predominantly responsible for specific posttranslational modifications of histone proteins, the chief organizational component of chromatin. As histone proteins bind DNA prior to transcription, their biochemical action plays a critical role in the regulation of gene expression and cellular differentiation. HDAC's are validated targets for a number of disease states, including cancer, neurodegenerative diseases, sickle-cell anemia, muscular dystrophy, and HIV. There are 11 known HDAC isoforms, which are divided into four subclasses depending on sequence homology and organization. Medical research has focused largely on small molecules which bind to the $Zn^{2+}$ centered class I and II HDACs. There are currently two HDAC inhibitors on the market, Vorniostat and Romidepsin. Both are approved for treatment of T-cell lymphoma. They are both also pan active inhibitors showing very little specificity of binding to HDAC subclasses. Because of this lack of specificity they have a number of side effects. In recent years there has been much effort in pharmaceutical companies toward development of selective inhibitors. To date there are very few selective HDAC-8 inhibitors. The most potent and selective was developed by Pharamcyclic and has a potency of 10 nM and modest selectivity over HDAC-1 and HDAC-6. Inventors have discovered a selective inhibitor of the HDAC-8. The molecule contained a 1,2,3-triazole core with a C-4 phenyl, C-5 alkynyl phenyl, and N-1 phenyl alanine derived hydroxamic acid substituents.

Figure 2:
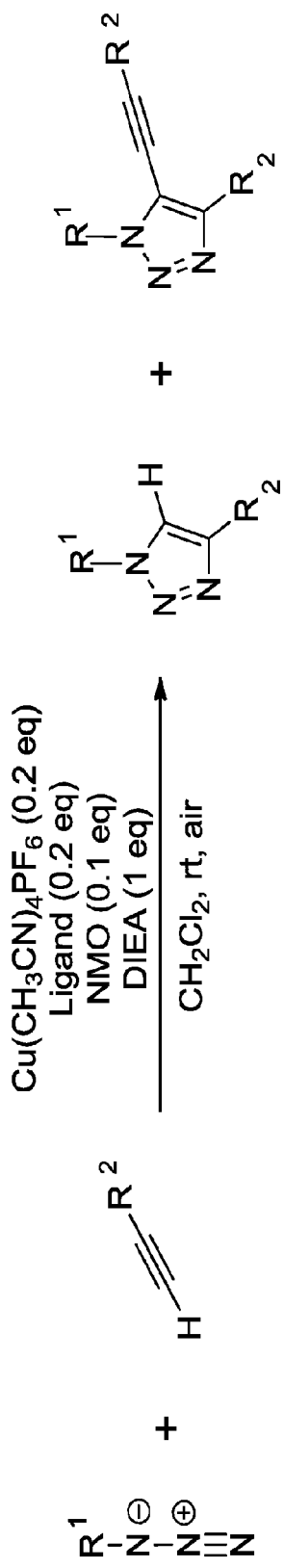
FIG. 2 is a schematic representation of methods for synthesizing the compounds described herein. Shown are methods based on the methods previously used in the art (old methodology) and the optimized synthetic route (new methodology) according to an embodiment of the synthesis method described herein.
Figure 2:
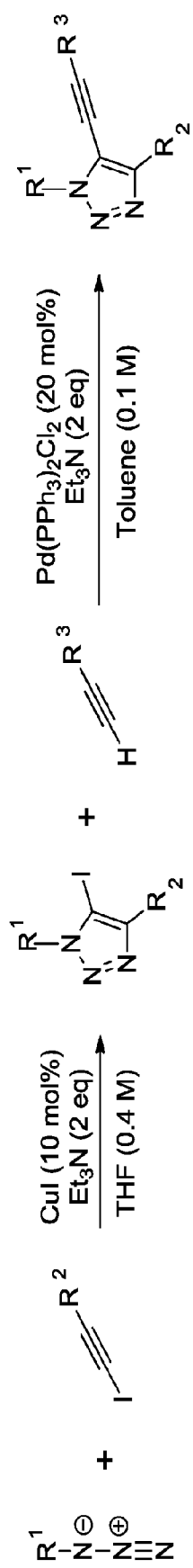

SAR libraries were synthesized to investigate substitution about the triazole core. In some examples, compounds were synthesized using the synthetic routes shown in FIG. 2. In one study, compound

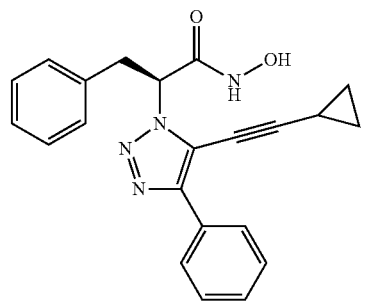 [SMILES: O=C(NO)[C@H](Cc1ccccc1)n1nnc(-c2ccccc2)c1C#CC1CC1]

was synthesized as outline in Scheme I.

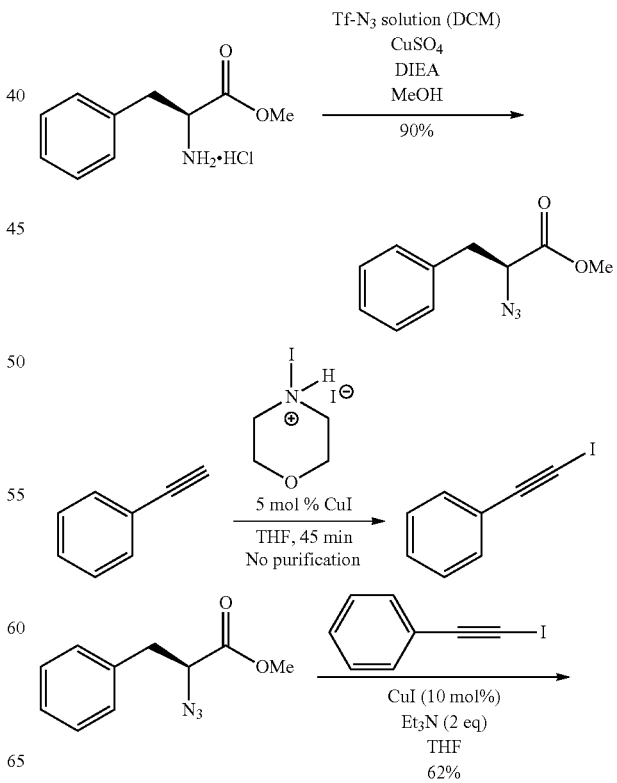

-continued

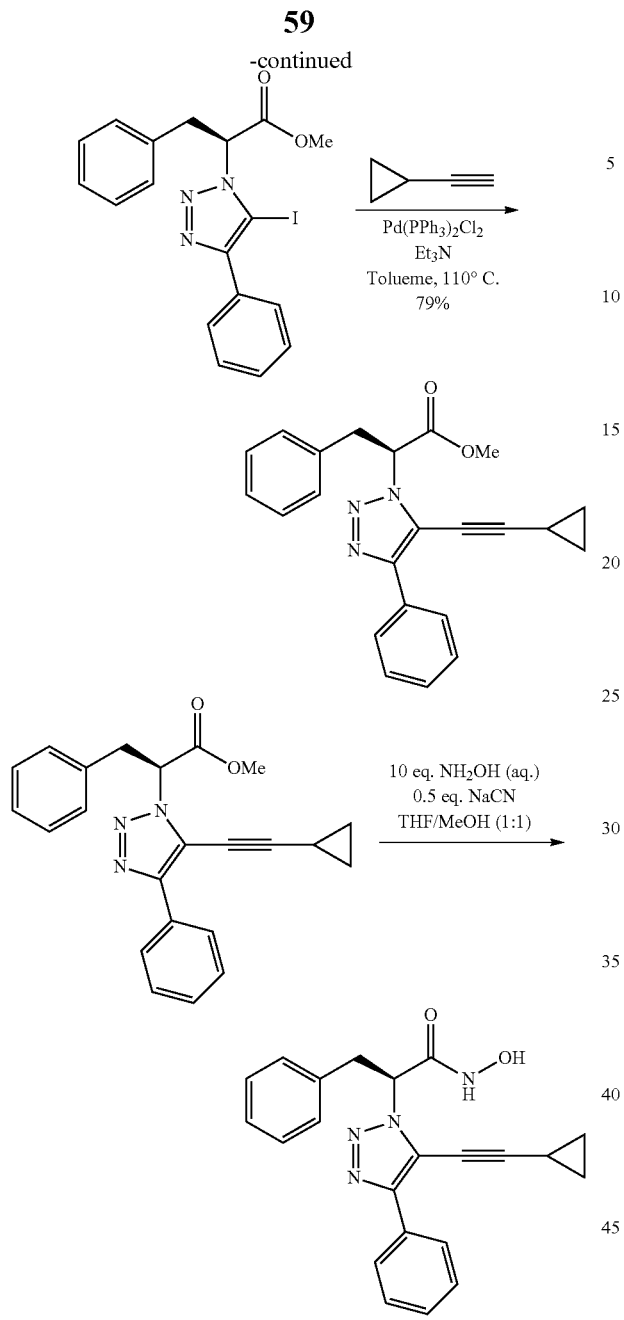
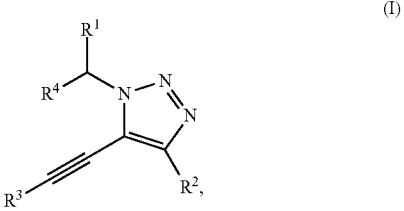

The HDAC assays were carried out as described in Bowers A, West N, Taunton J, Schreiber S L, Bradner J E, Williams R M Total Synthesis and Biological Mode of Action of Largazole: A Potent Class I Histone Deacetylase Inhibitor. *J. Am. Chem. Soc.* 2008, 130, 11219-11222. Assay results revealed that among the analogues tested a cyclopropane analog was the most active at 0.4 nM (>1000 fold selectivity). These results demonstrated that a small aliphatic group in the 5-position on the triazole can increase potency. Also, compounds with an L-phenylalanine moiety at the 3-position showed significant potency. To expand our understanding of how the molecule interacts with the binding pocket of HDAC 8 and to understand our preliminary SAR, molecular modeling was carried out. The phenyl group from the original amino methyl ester fits snuggly into the Zn binding site and the alkynyl phenyl group sits flat in a hydrophobic groove. In summary, the inventors have developed a potent and highly selective small molecule which inhibits HDAC-8 at approximately 500 pM with over 1000-fold selectivity over HDAC-6 and significantly greater selectivity for all other HDACs. To inventors' knowledge, to date there are no compounds with this level of potency and selectivity.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:
1. A compound of formula (I):

(I)

wherein:
R$^1$ is optionally substituted linear or branched alkyl, optionally substituted linear or branched alkenyl, optionally substituted linear or branched alkynyl, optionally substituted cyclyl, optionally substituted heterocycicyl, optionally substituted aryl, optionally substituted heteroaryl, halogen, CN, CF$_3$, C(O)R$^5$, CO$_2$R$^5$, C(O)N(R$^6$)$_2$, OR$^5$, SR$^5$, SOR$^5$, SO$_2$R$^5$, SSR$^5$ N(R$^6$)$_2$, NHR$^6$, NR$^6$C(O)R$^5$, or NO$_2$, each of which can be optionally substituted, wherein the backbone of alkyl, alkenyl, or alkynyl optionally comprises one or more heteroatoms, and wherein the carbon to which R$^1$ is attached has the S stereochemistry;

R$^2$ is optionally substituted linear or branched alkyl, optionally substituted linear or branched alkenyl, optionally substituted linear or branched alkynyl, optionally substituted cyclyl, optionally substituted heterocycicyl, optionally substituted aryl, optionally substituted heteroaryl, halogen, CN, CF$_3$, C(O)R$^5$, CO$_2$R$^5$, C(O)N(R$^6$)$_2$, OR$^5$, SR$^5$, SOR$^5$, SO$_2$R$^5$, OSO$_2$R$^5$, SSR$^5$, N(R$^6$)$_2$, NHR$^6$, NR$^6$C(O)R$^5$, or NO$_2$, each of which can be optionally substituted, and wherein the backbone of alkyl, alkenyl, or alkynyl optionally comprises one or more heteroatoms;

$R^3$ is H, optionally substituted linear or branched alkyl, optionally substituted linear or branched alkenyl, optionally substituted linear or branched alkynyl, optionally substituted cyclyl, optionally substituted heterocycicyl, or optionally substituted aryl, optionally substituted heteroaryl;

$R^4$ is —C(O)$R^7$, —NH—P(O)O$R^5$—$R^5$, —SO$_2R^5$, —SO$_2$N($R^6$)$_2$, —SO$_2$N$R^6$O$R^5$, or —S$R^5$;

$R^5$ is independently for each occurrence H, optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, wherein the backbone of alkyl, alkenyl, or alkynyl optionally comprises one or more heteroatoms;

$R^6$ is independently for each occurrence H, optionally substituted linear or branched alkyl, optionally substituted linear or branched alkenyl, optionally substituted linear or branched alkynyl, optionally substituted cyclyl, optionally substituted heterocyclcyl, optionally substituted aryl, optionally substituted heteroaryl, C(O)$R^5$, CO$_2R^5$, or SO$_2R^5$, each of which can be optionally substituted, wherein the backbone of alkyl, alkenyl, or alkynyl optionally comprises one or more heteroatoms;

$R^7$ is independently for each occurrence optionally substituted alkyl, wherein said alkyl does not include an heteroatom in the backbone, N$R^6$O$R^5$, amino, —C(O)N($R^6$)$_2$, optionally substituted cyclyl, optionally substituted aryl; optionally substituted heteroaryl; optionally substituted alkylamino, where two substituents together with the nitrogen do not form a ring, optionally substituted arylamino, or optionally substituted heteroarylamino; and a hydrate, salt, or solvate thereof.

2. The compound of claim 1, wherein $R^1$ is selected from the group consisting of linear or branched $C_1$-$C_{10}$ alkyl, aryl, —CH$_2$-aryl, and —CH$_2$-heteroaryl, each of which can be optionally substituted.

3. The compound of claim 2, wherein $R^1$ is selected from the group consisting of benzyl, 2-propyl, 1H-indol-3-yl-methyl, phenyl, and indol-3-yl-methyl.

4. The compound of claim 1, wherein $R^2$ is linear or branched $C_1$-$C_{10}$ alkyl, cyclyl, heterocyclyl, aryl, or heteroaryl, each of which can be optionally substituted.

5. The compound of claim 4, wherein $R^2$ is phenyl.

6. The compound of claim 1, wherein $R^3$ is $C_1$-$C_{10}$alkyl; aryl; heteroaryl; cyclyl; heterocyclyl; $C_1$-$C_6$alkyl substituted with aryl, heteroaryl, cyclyl, heterocyclyl, O$R^5$, S$R^5$, or —OSO$_2R^5$, wherein $R^5$ is H, alkyl, alkenyl, alkynyl, aryl, heteroaryl, cyclyl, heterocyclyl, and each of which can be optionally substituted.

7. The compound of claim 6, wherein $R^3$ is 2-phenyl ethyl; phenylthio methyl; 4-fluoro phenyl; phenoxy methyl; 4-methoxy phenyl; 4-bromo phenyl; 4-t-butyl phenyl; phenyl; 4-cyano phenyl; 2-pyridinyl; 3-pyridinyl; 2-pyranyloxy ethyl; cyclopropyl; isoindoline-1,3-dionyl methyl; 4-phenyl phenyl; 4-ethyl phenyl; cyclopentyl methyl; 3-methoxy phenyl; 4-(N,N-dimethylamino) phenyl; 3-chloro phenyl; 3,5-dimethoxy phenyl; 2,4,5-trimethyl phenyl; 2-methoxy phenyl; 2-methyl-4-methoxyphenyl;4-acerylamino phenyl; 4-chloro phenyl; 4-methyl-phenylsulfonyloxy methyl; and phenylsulfonyloxy methyl.

8. The compound of claim 7, wherein $R^3$ is phenyl or cyclopropyl.

9. The compound of claim 1, wherein $R^7$ is NHO$R^5$; —SO$_2$NHO$R^5$; optionally substituted phenylamino; optionally substituted aza-aryl amino; or optionally substituted $C_1$-$C_6$ alkyl.

10. The compound of claim 1, wherein $R^4$ is —C(O)NHOH, —CF$_3$, —SO$_2$NHOH, —C(O)CH$_2$OH, —C(O)CH$_2$SH, acetyl (—C(O)CH$_3$), —C(O)CH$_2$CH$_3$, 2-aminophenylamino-carbonyl; 2-hydroxy-phenylamino-carbonyl; thiazolyl-amino carbonyl; oxazolylamino carbonyl; 4,5-dihydro-oxazolylamino carbonyl; or oxiranyl carbonyl.

11. The compound of claim 10, wherein $R^4$ is hydroxamic acid (—C(O)NHOH).

12. The compound of claim 1, wherein the compound is a compound of formula (IB):

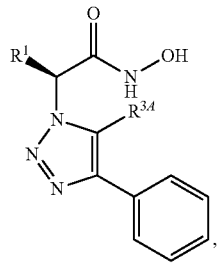

(IB)

wherein:

$R^1$ is benzyl, 2-propyl, 1H-indol-3-yl-methyl, or phenyl; and $R^{3A}$ is selected from

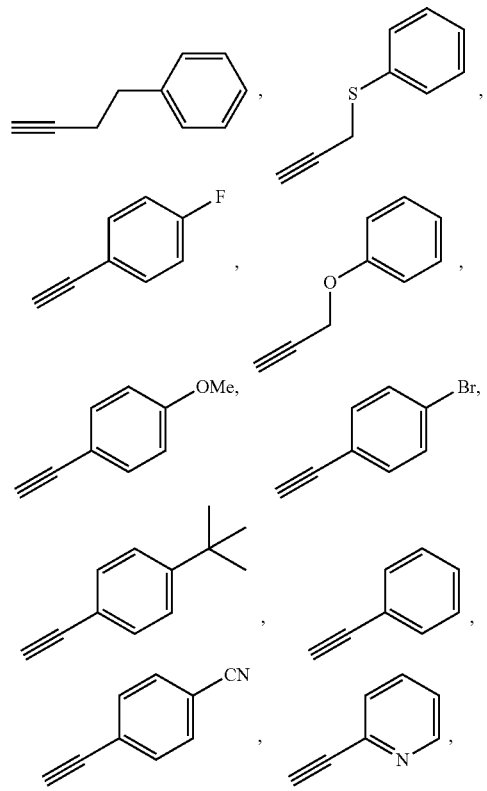

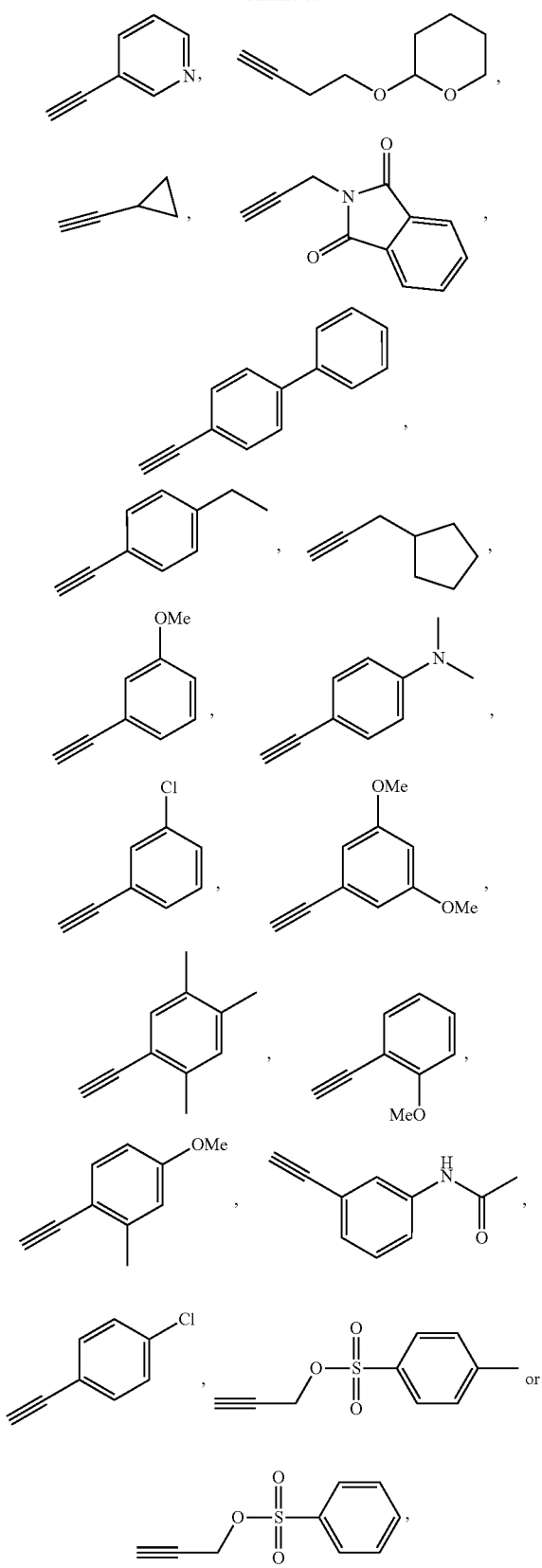

wherein R³⁴ is connected via the carbon on the terminal end of the alkyne shown in the structures.

13. The compound of claim 12, wherein the compound is

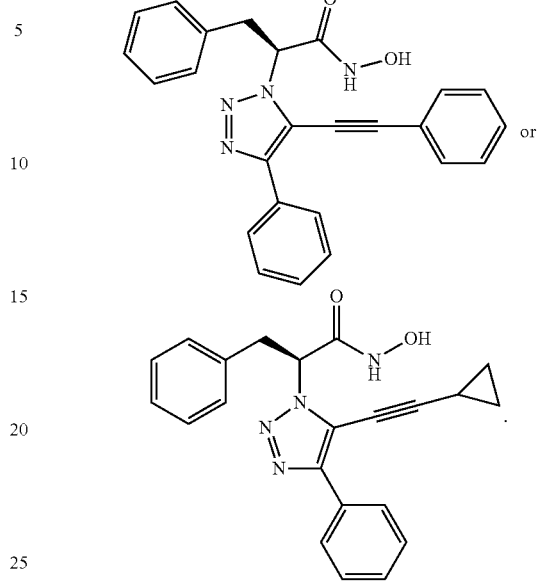

14. A pharmaceutical composition comprising a compound of claim 1 and a pharmaceutically acceptable diluent, excipient, or carrier.

15. A method of treating cancer, the method comprising administering a therapeutically effective amount of a compound of claim 1 to a subject having cancer.

16. The method of claim 15, wherein the cancer is selected from the group consisting of adenocarcinoma; adult T-cell leukemia/lymphoma; AIDS-associated leukemia ; basal cell carcinoma; biliary tract cancer; bladder cancer; blastoma; brain cancer, glioblastomas, medulloblastomas breast cancer; cervical cancer; choriocarcinoma; chronic myelogenous leukemia; colon cancer; colorectal cancer; endometrial carcinoma; esophageal cancer; esticular cancer; gastric cancer; gastrointestinal cancer; Glioblastoma; hairy cell leukemia; hematological neoplasms, acute lymphocytic and myelogenous leukemia; Hodgkin's and non-Hodgkin's lymphoma; intraepithelial neoplasms, Bowen's disease and Paget's disease; Leukemia; liver cancer, hepatic carcinoma and hepatoma; lung cancer; lymphomas, Hodgkin's disease and lymphocytic lymphomas; melanoma; multiple myeloma; neuroblastomas; non-small cell lung cancer; oral cancer squamous cell carcinoma; ovarian cancer, cancer arising from epithelial cells, stromal cells, germ cells and mesenchymal cells; pancreatic cancer; prostate cancer; rectal cancer; renal cancer, adenocarcinoma, kidney cancer, and Wilms' tumor; salivary gland carcinoma; sarcomas leiomyosarcoma, rhabdomyosarcoma, liposarcoma, fibrosarcoma, and osteosarcoma; skin cancer, melanoma, Merkel cell carcinoma, Kaposi's sarcoma, basal cell carcinoma, and squamous cell cancer; small-cell lung cancer; squamous cell cancer; T-cell acute lymphoblastic leukemia/lymphoma; T-cell lymphoma; testicular cancer, germinal tumors, seminoma, non-seminoma (teratomas, choriocarcinomas), stromal tumors, and germ cell tumors; thyroid cancer thyroid adenocarcinoma and medullar carcinoma; vulval cancer, and any combinations thereof.

17. The method of claim 16, wherein the cancer is T-cell lymphoma, leukemia, or neuroblastoma.

18. The method of claim 15, further comprising administering one or more additional anti-cancer therapy to the subject.

* * * * *